(12) United States Patent
Gunton

(10) Patent No.: US 8,518,419 B2
(45) Date of Patent: Aug. 27, 2013

(54) METHOD OF TREATING DIABETES

(75) Inventor: Jenny Gunton, Riverview (AU)

(73) Assignee: Garvan Institute of Medical Research (AU)

( * ) Notice: Subject to any disclaimer, the term of this patent is extended or adjusted under 35 U.S.C. 154(b) by 515 days.

(21) Appl. No.: 12/515,722

(22) PCT Filed: Nov. 20, 2007

(86) PCT No.: PCT/AU2007/001783
§ 371 (c)(1),
(2), (4) Date: Jan. 29, 2010

(87) PCT Pub. No.: WO2008/061299
PCT Pub. Date: May 29, 2008

(65) Prior Publication Data
US 2010/0143333 A1  Jun. 10, 2010

Related U.S. Application Data

(60) Provisional application No. 60/880,159, filed on Jan. 12, 2007.

(30) Foreign Application Priority Data

Nov. 21, 2006 (AU) .............................. 2006906499

(51) Int. Cl.
*A61K 45/00* (2006.01)
*A61K 47/00* (2006.01)

(52) U.S. Cl.
USPC ...................................................... 424/278.1

(58) Field of Classification Search
None
See application file for complete search history.

(56) References Cited

FOREIGN PATENT DOCUMENTS

| WO | WO 2005/115379 A2 | 12/2005 |
|----|-------------------|---------|
| WO | WO 2007/039731 A1 | 4/2007  |

OTHER PUBLICATIONS

Emamaulle, J.A., et al. Diabetes. 2005;54:2541-2548.*
Jiang, Y., et al. Leukemia. 2005;19:1239-1247.*
Akakura, N., et al. Cancer Res. 2001;61:6548-6554.*
Miao, G., et al. Am. J. Transplant. 2006;6:2636-2643.*
Moritz, W., et al. FASEB J, 2002;16:745-747.*
Cheng, K., et al. J. Clin. Invest. 2010;120(6):2171-2183).*
Girgis, C.M., et al. Trends in Endocrin. Metab. 2012;23(8):372-380.*
Guo, M., et al. Apoptosis 2006;11(1):67-77.*
Cameron et al.; "Neurovascular dysfunction in diabetic rats Potential contribution of autoxidation and free radicals examined using transition metal chelating agents"; 1995; *J. Clin. Invest.*; vol. 96, pp. 1159-1163.
Catrina et al.; "Hyperglycemia regulates hypoxia-inducible factor-1α protein stability and function"; 2004; *Diabetes*; vol. 53, pp. 3226-3232.
Fernandez-Real, et al.; "Cross-talk between iron metabolism and diabetes"; 2002; *Diabetes*; vol. 51, No. 8, pp. 2348-2354.
Piret, et al.; "$CoCl_2$, a chemical inducer of hypoxia-inducible factor-1, and hypoxia reduce apoptotic cell death in hepatoma cell line HepG2"; 2002; Ann. N.Y. Acad. Sci.; vol. 973, pp. 443-447.
Roth et al.; "The transcription factors HIF-I and HNF-4and the coactivator p300 are involved in insulin-regulated glucokinase gene expression via the phosphatidylinositol 3-kinase/protein kinase B pathway"; 2004; *J. Biol. Chem.*; vol. 279, No. 4, pp. 2623-2631.
Zelzer; et al. "Insulin induces transcription of target genes through the hypoxia inducible factor HIF-1α/ARNT"; 1998; *EMBO J.*; vol. 17, No. 17, pp. 5085-5094.

* cited by examiner

*Primary Examiner* — Gerald R Ewoldt
(74) *Attorney, Agent, or Firm* — Kilpatrick Townsend & Stockton LLP

(57) ABSTRACT

The present invention relates to a method for treating a subject having or at risk of a diabetes-related disorder. In a preferred embodiment, the method involves increasing the level or activity of Hypoxia Induced Factor 1 (HIF-1 α) in pancreatic-β-cells or insulin-sensitive tissues in the subject by administering to the subject an inhibitor of a protein that decreases the level or activity of HIF-1α. The present invention also relates to a method of transplanting pancreatic islet cells in a subject.

12 Claims, 7 Drawing Sheets

METHOD OF TREATING DIABETES

CROSS-REFERENCE TO RELATED APPLICATIONS

Figure 1:
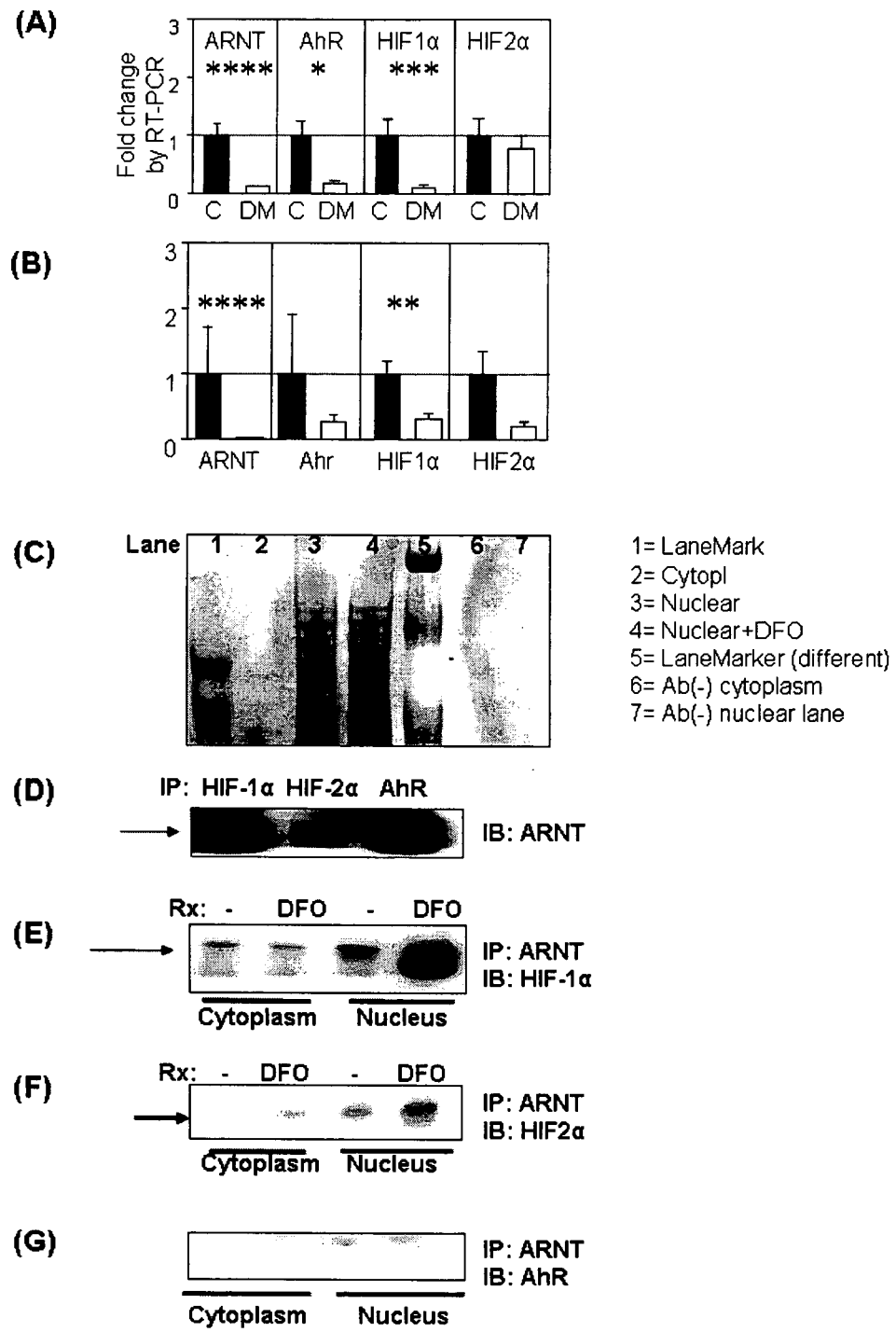

The present application is the U.S. National Stage entry under §371 of International Application No. PCT/AU2007/001783, filed Nov. 20, 2007 which claims benefit of priority of Australian Application No. 2006906499, filed Nov. 21, 2006 and of U.S. Application No. 60/880,159, filed Jan. 12, 2007; the disclosures of each are hereby incorporated by reference in their entirety for all purposes.

FIELD OF THE INVENTION

The present invention provides a method for treating a subject having or at risk of a diabetes-related disorder. The present invention also provides a method of transplanting pancreatic islet cells in a subject.

BACKGROUND OF THE INVENTION

Diabetes involves dysfunction of the pancreatic islet cells. In the case of type 1 diabetes, also referred to as insulin dependent diabetes mellitus (IDDM), dysfunction is initiated in the event of an immunological challenge. In the case of type 2 diabetes, also referred to as non-insulin dependent diabetes mellitus (NIDDM), islet dysfunction occurs upon exposure to a homeostatic challenge. Diabetes is associated with total β-cell mass, as well as the properties of individual β-cells.

Type 1 Diabetes and Insulitis. Type 1 diabetes is a chronic autoimmune disease in which insulin-producing cells (β-cells) within the pancreatic islets of Langerhans are selectively targeted and destroyed by an infiltrate of immunological cells. This infiltrate causes an inflammatory affect on the islets, known as insulitis.

The development of type 1 diabetes is associated with an initial genetic susceptibility, although this susceptibility is insufficient for development of the disease. In susceptible individuals, it has been hypothesized that a triggering event leads to an active autoimmunity attack against β-cells, resulting in insulitis, islet β-cell dysfunction, diminished insulin secretion, and ultimately, β-cell destruction. β-cells comprise the majority of pancreatic islet cells. Overt type 1 diabetes onset characterised by hyperglycemia may not be diagnosed until years after an initial triggering event, at which point most of the pancreatic β-cells are destroyed. When overt diabetes is first recognised, some residual insulin production remains, as demonstrated by the presence of the connecting peptide (C peptide) of proinsulin in the serum. However, the individual usually requires injections of exogenous insulin. Complete β-cell destruction is determined when C peptide can no longer be detected in the circulation after stimulation with glucose or arginine.

The initiating factor(s) and specific sequence of events leading to type 1 diabetes, including the relative importance of different cell types and cytokines, are still widely debated. It is generally accepted that insulitis leading to type 1 diabetes involves cellular migration and infiltration of T lymphocytes, macrophages, and dendritic cells within the pancreatic islets. Immune stimulation of the newly infiltrated cells, and cytokine-regulated effects of such infiltration result in inflammation and β-cell destruction (Mandrup-Poulsen, 1996). Interleukin 1β (IL 1β), alone or in combination with tumor necrosis factor α (TNFα) and interferon γ (IFN γ), exhibits cytotoxicity toward β-cells in vitro (Cetkovic et al., 1994). This cytotoxicity is partly mediated through induction of free radicals such as nitric oxide (NO), the production of which is catalysed by inducible nitric oxide synthase (iNOS). NO released in β-cells leads to nuclear DNA fragmentation and apoptosis, a result which can be partially prevented by iNOS blockers. However, the blockers may not be used in vivo because of the various roles of NO in other organ systems.

Conventional treatment protocols for type 1 diabetes comprise regular administration, of insulin. Preferably, the insulin is administerered by injection. Other protocols have been suggested which include such immunomodulatory and immunosuppressive agents as levamisol, theophyllin, thymic hormones, ciamexone, antithymocyte globulin, interferon, cyclosporin, nicotinamide, gamma globulin infusion, plasmapheresis or white cell transfusion. Although these protocols may delay onset of type 1 diabetes, some undesirable side effects are observed. Treatment protocols after onset of type 1 diabetes are particularly problematic, since by the time diabetes is diagnosed in humans, insulitis has already progressed dramatically, resulting in a β-cell loss of more than 80%. Islet cell transplantation is a viable treatment for type 1 diabetes although graft rejection is still a major problem. Survival of transplanted islets requires effective immunosuppression, to block the immune response that leads to graft rejection. However, it is thought that the majority of islet death occurs in the first week post-transplant with up to 70% of β-cells also undergoing apoptotic cell death triggered by nonimmunological factors, such as hypoxia.

Type 2 Diabetes. Type 2 diabetes often occurs in the face of normal, or even elevated levels of insulin. The condition appears to arise from β-cell dysfunction, usually combined with impaired ability of tissues to respond appropriately to insulin (i.e. insulin resistance), which challenges the homeostasis of blood glucose. Over time, many individuals with type 2 diabetes show decreased insulin production and require supplemental insulin to maintain blood glucose control, especially during times of stress or illness.

Conventional treatments for type 2 diabetes have not changed substantially in many years, and have significant limitations. While physical exercise and a reduction in caloric intake can improve the condition, compliance with such regimens is generally poor. Oral anti-diabetic drugs—the sulfonylureas, biguanides (metformin), thiazolidediones, α-glucosidase inhibitors (acarbose, miglitol), meglitinides (nateglinide, repaglinide) and exenatide can also be used to maintain blood glucose levels. Insulin therapy may also be used as an adjunct or alternative to oral medication therapy.

SUMMARY OF THE INVENTION

The present inventors have now made the surprising finding that the transcription factor hypoxia induced factor (HIF)-1α is needed for normal β-cell function, that is, glucose stimulated insulin secretion. In addition, the present inventors have also shown that inducing HIF-1α in islet cells prior to transplantation improved graft survival.

Accordingly, the present invention provides a method for treating a subject having or at risk of a diabetes-related disorder, the method comprising increasing the level or stability of HIF-1α activity in pancreatic β-cells or insulin-sensitive tissues in the subject.

In one embodiment of the invention, the diabetes-related disorder is selected from the group consisting of insulitis, type 1 diabetes, type 2 diabetes, impaired glucose tolerance, gestational diabetes, insulin resistance and β-cell dysfunction.

In a further preferred embodiment of the invention, the level or stability of HIF-1α activity is increased by administering to the subject an inhibitor of a protein that mediates degradation of HIF-1α.

In one embodiment of the invention, the protein that mediates degradation of HIF-1α is a Von Hippel-Lindau protein (VHL).

In a further preferred embodiment, the inhibitor of a protein that mediates degradation of HIF-1α is an antisense nucleic acid, ribozyme, PNA, interfering RNA, siRNA, microRNA or antibody. Preferably, the inhibitor is a siRNA.

In a further preferred embodiment of the invention, the level or stability of HIF-1α activity is increased by administering to the subject a chelating agent. Preferably, the chelating agent is an iron chelator.

The iron chelator is preferably selected from the group consisting of desferrioxamine (DFO), ferrioxamine, trihydroxamic acid, CP94, EDTA, desferrioxamine hydroxamic acids, deferoxamine B (DFO) as the methanesulfonate salt, also known as desferrioxamine B mesylate (DFOM), desferal from Novartis (previously Ciba-Giegy), apoferritin, CDTA (trans-1,2-diaminocyclohexane-N,N,N',N'-tetraacetic acid), and DTPA (diethylenetriamine-N,N,N',N'',N''-penta-acetic acid) and cobaltous ions.

In a preferred embodiment, the iron chelator is desferrioxamine (DFO).

In another embodiment of the invention, the level of HIF-1α is increased by administering to the subject a HIF-1α polypeptide or an active fragment thereof, or a polynucleotide encoding HIF-1α polypeptide or an active fragment thereof.

In a one embodiment of the invention, the polynucleotide is a vector encoding a HIF-1α polypeptide or active fragment thereof. Preferably the vector is a viral vector.

In a further preferred embodiment of the invention, the vector is within a cell. Preferably, the cell is a pancreatic n-cell. More preferably the cell is autologous.

In a further preferred embodiment of the invention, the HIF-1α polypeptide or active fragment thereof is administered with a pharmaceutically acceptable carrier.

The present invention also provides a method of transplanting pancreatic islet cells in a subject, the method comprising administering islet cells to a subject and increasing the level or activity of HIF-1α in the islet cells.

In one embodiment of the invention, the level or stability of HIF-1α in increased in the islet cells before transplantation.

In another embodiment of the invention, the level or stability of HIF-1α is increased in the islet cells after transplantation.

In a further preferred embodiment of the invention, the level or stability of HIF-1α activity is increased by administering to the subject an inhibitor of a protein that mediates degradation of HIF-1α.

In one embodiment of the invention, the protein that mediates degradation of HIF-1α is VHL.

In a further preferred embodiment of the invention, the inhibitor of a protein that mediates degradation of HIF-1α is an antisense nucleic acid, ribozyme, PNA, interfering RNA, siRNA, microRNA or antibody. Preferably, the inhibitor is a siRNA.

In a further preferred embodiment of the invention, the level or stability of HIF-1α activity is increased by administering to the subject an iron chelator.

The iron chelator is preferably selected from the group consisting of desferrioxamine (DFO), ferrioxamine, trihydroxamic acid, CP94, EDTA, desferrioxamine hydroxamic acids, deferoxamine B (DFO) as the methanesulfonate salt, also known as desferrioxamine B mesylate (DFOM), desferal from Novartis (previously Ciba-Giegy), apoferritin, CDTA (trans-1,2-diaminocyclohexane-N,N,N',N'-tetraacetic acid), and DTPA (diethylenetriamine-N,N,N',N'',N''-penta-acetic acid) and cobaltous ions.

In a preferred embodiment, the iron chelator is desferrioxamine (DFO).

In another embodiment of the invention the level of HIF-1α is increased by administering to the subject a HIF-1α polypeptide or an active fragment thereof, or a polynucleotide encoding HIF-1α polypeptide or an active fragment thereof.

In a one embodiment of the invention, the polynucleotide is a vector encoding a HIF-1α polypeptide or active fragment thereof. Preferably the vector is a viral vector.

In a further preferred embodiment of the invention, the vector is within a cell. Preferably, the cell is a pancreatic β-cell. More preferably the cell is autologous.

In a further preferred embodiment of the invention, the HIF-1α polypeptide or active fragment thereof is administered with a pharmaceutically acceptable carrier.

The present invention also provides a method for the treatment of a diabetes-related disorder, which involves the method of transplantation according to the methods of the invention. Preferably, the diabetes-related disorder is type 1 diabetes.

The methods of the invention can be performed on a range of different subjects. Preferably, the subject is a mammal. More preferably, the subject is human.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

As will be apparent, preferred features and characteristics of one aspect of the invention are applicable to other aspects of the invention.

The invention is hereinafter described by way of the following non-limiting Examples and with reference to the accompanying figures.

BRIEF DESCRIPTION OF THE ACCOMPANYING DRAWINGS

FIG. 1: HIF-1α is present in human and mouse islets and in Min6 cells, and is decreased in islets from people with diabetes. (A) By real-time PCR, expression of ARNT and HIF-1α were decreased by 90% in islets from people with type 2 diabetes (white bars) compared to control subjects (black bars). Expression of AhR was also decreased. (B) In islets isolated from mice with β-cell specific knockout of ARNT, HIF-1α expression was significantly decreased. (C) Following ARNT affinity-purification, a band corresponding to HIF-1α was present in Min6 cells basally and following treatment with DFO. (D) ARNT co-immunoprecipitated with HIF-1α, HIF-2α and AhR in Min6 cells. (E) HIF-1α co-immunoprecipitated with ARNT, both in the basal state and following treatment with DFO. (F) HIF-2α also co-immunoprecipitated with ARNT. (G) AhR did not co-immunoprecipitate with ARNT.

Figure 2:
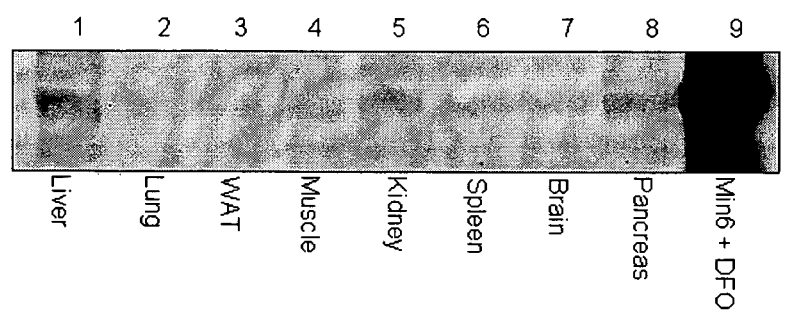

FIG. 2: HIF-1αprotein is present in a range of normal tissues, and in Min6 cells. Tissues were isolated from wild-type mice and immediately snap-frozen in liquid nitrogen. HIF-1α protein was detectable following immunoprecipitation in liver, muscle, kidney, pancreas and in Min6 cells, used as the positive control.

Figure 3:
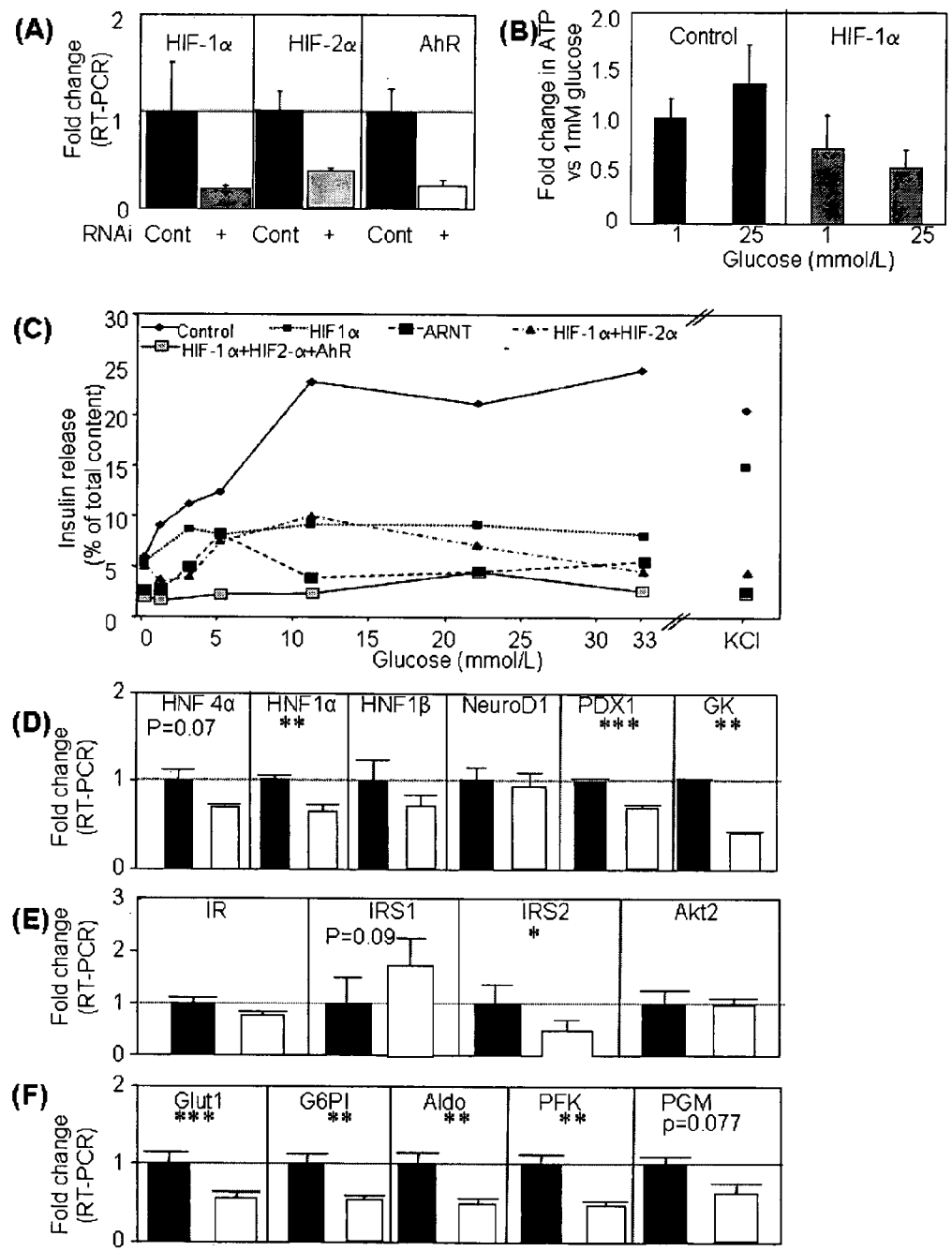

FIG. 3: Knockdown of HIF-1α protein markedly impairs glucose stimulated ATP generation, glucose stimulated insulin secretion and gene expression in Min6 cells. (A) RNAi treatment for 48 hours produced significant decreases in expression of HIF-1α, HIF-2α and AhR (p<0.01, 0.01 and 0.05 respectively). (B) In control cells, increasing glucose concentration from 1 mM to 25 mM caused a significant increase in cellular ATP concentration (p<0.05) but this was completely blocked in cells treated with RNAi directed against HIF-1α. (C) Min6 cells treated with scrambled control RNAi sequences have normal glucose stimulated insulin secretion (GSIS). Treatment with HIF-1α RNAi severely impaired GSIS, similar to that seen with ARNT RNAi. Addition of HIF-2α or HIF-2α+AhR RNAis did not cause significant further decreases in GSIS. HIF-2α RNAi alone or AhR RNAi alone produced ~25% impairment in GSIS (data not shown). (D) HIF-1α RNAi caused significant decreases in gene expression in Min6 cells with decreased expression of the MODY genes HNF1α, PDX-1 and glucokinase (GK) and a trend to decreased HNF4α. (E) Expression of IRS-2 was significantly decreased by HIF-1α RNAi and (F) Expression of GLUT1, G6PI, aldolase (Aldo) and phosphofructokinase (PFK) mRNAs were all significantly decreased by HIF-1α RNAi.

Figure 4:
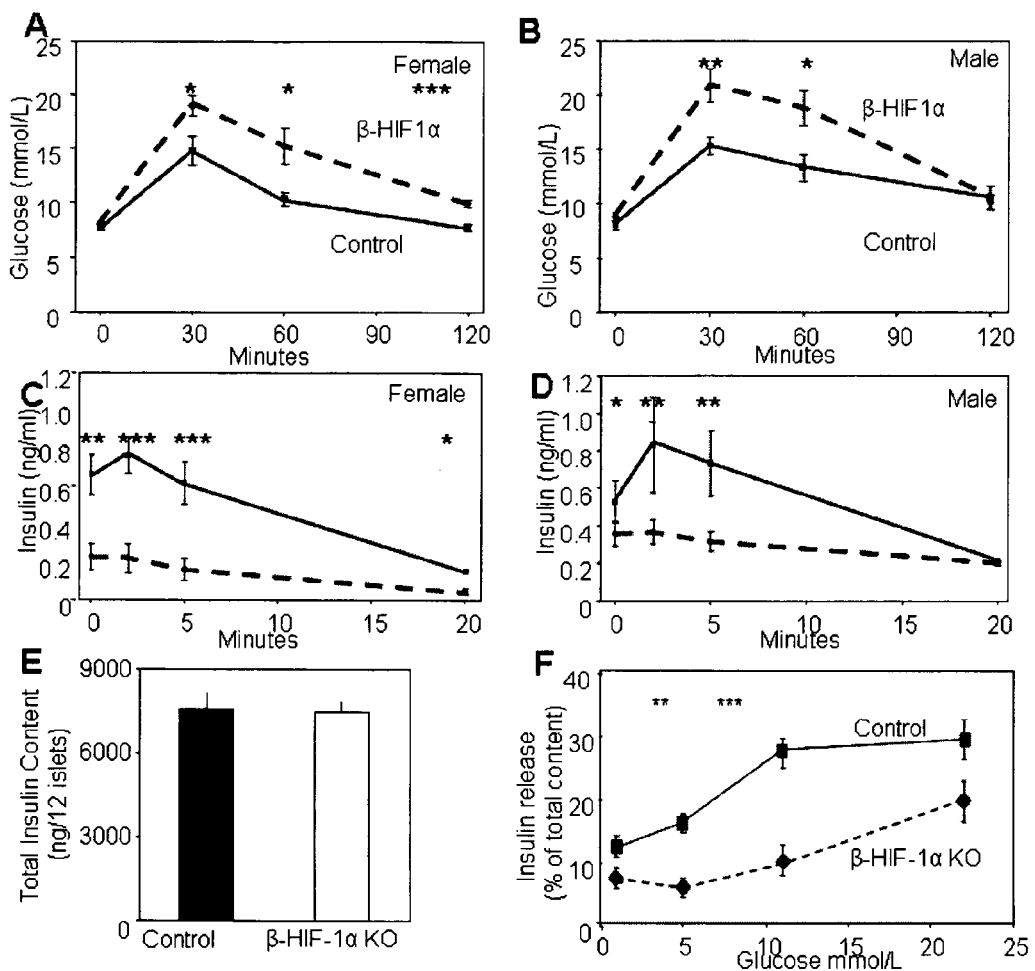

FIG. 4: Glucose tolerance is abnormal in β-HIF-1α mice. (A) Female β-HIF-1α mice have marked glucose intolerance following intraperitoneal glucose tolerance testing (2 g/kg). (B) Male β-HIF-1α mice also have significantly worse glucose intolerance. The glucose intolerance due to a β-cell defect, demonstrated by severely impaired GSIS in both female (C) and male (D) β-HIF-1α mice. (E) Total insulin content was unchanged in islets isolated from β-HIF-1α mice compared to their controls. Despite this, the islets in vitro show marked impairment in GSIS, shown in (F).

Figure 5:
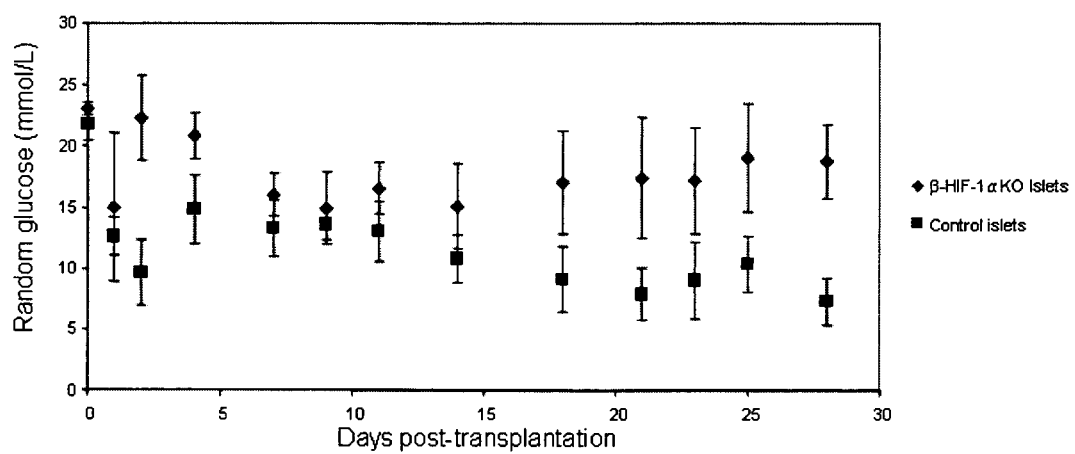

FIG. 5: Islets from β-HIF-1α mice were unable to control glucose post-transplantation. Islets were isolated from mice and transplanted into diabetic SCID mice in a 1 donor: 1 recipient ratio. Despite similar numbers of islets being isolated from β-HIF-1α and control mice, and identical total insulin content, islets from β-HIF-1α mice were unable to control glucose.

Figure 6:
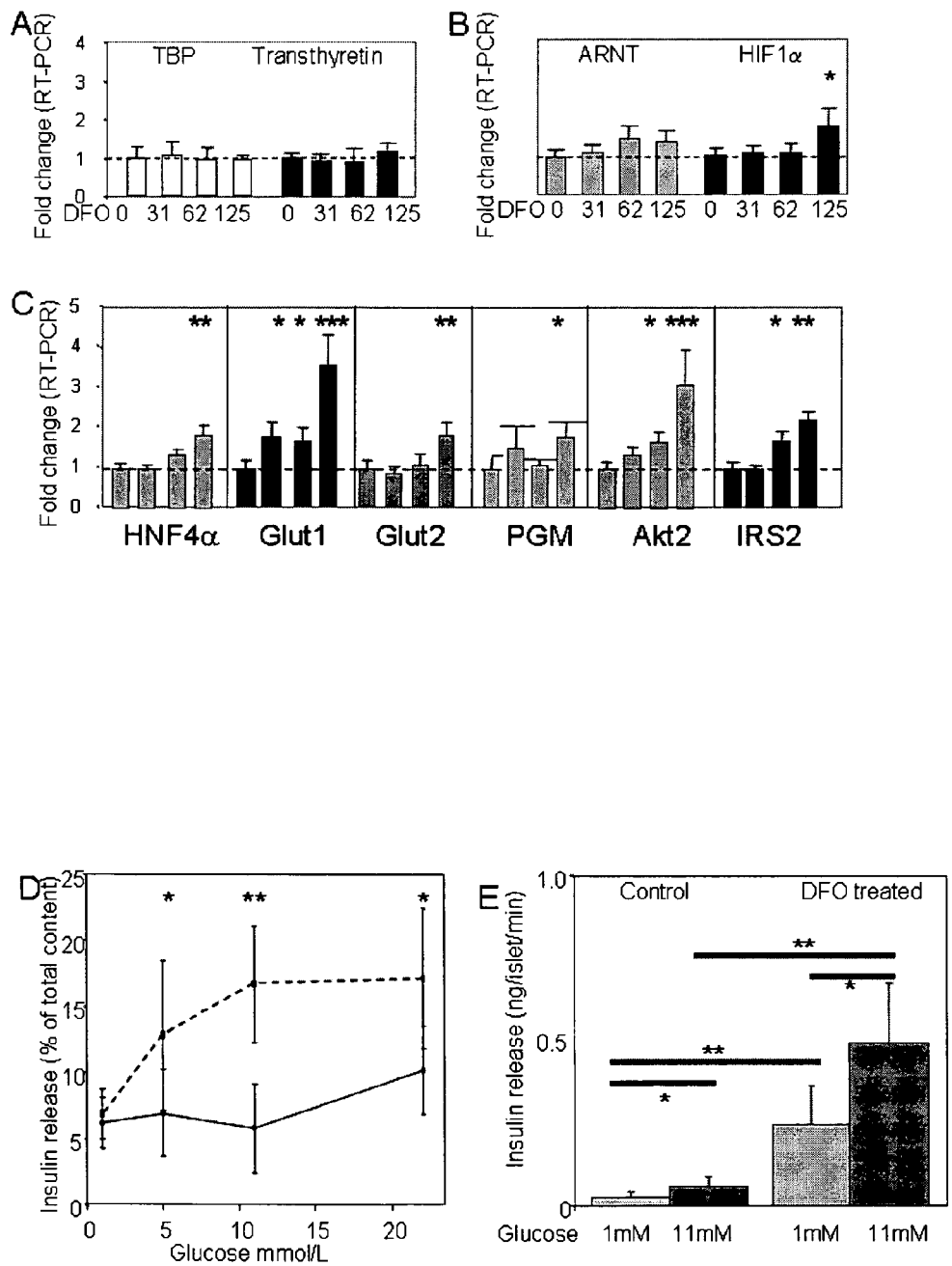

FIG. 6: Increasing HIF-1α protein by treatment with DFO at the concentrations shown for 4 hours markedly improves II-cell function. (A) DFO treatment did not alter expression of the house-keeping genes TATA-box binding protein (TBP) or transthyretin, or (B) increase expression of ARNT. However, at the highest dose, mRNA for HIF-1α showed increased expression. (C) DFO treatment significantly increased expression of several genes known to be important for normal β-cell function including HNF4α, GLUT1, GLUT2, phosphoglucomutase (PGM), IRS-2 and Akt2 (D) Human islets cells treated with DFO for 4 hours showed markedly improved GSIS. (E) In accord with the increased insulin release, DFO treatment was associated with increased ATP concentrations (E). Black lines indicate which columns/groups are being compared for the significance levels.

Figure 7:
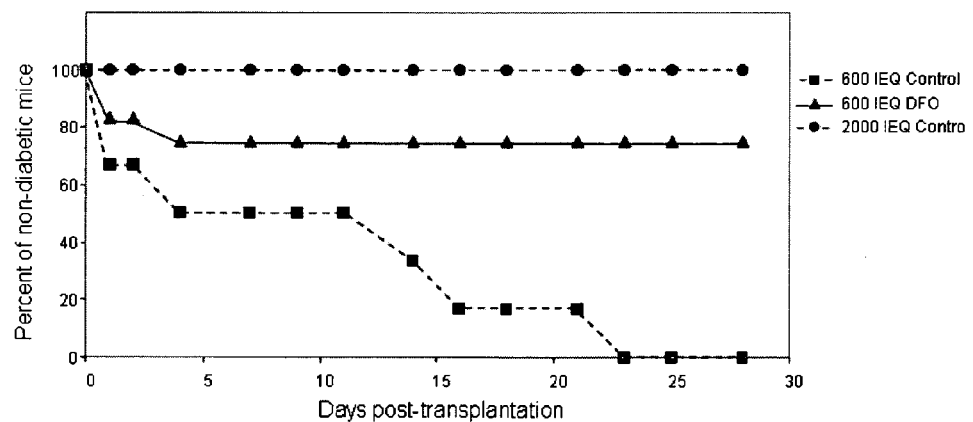
Figure 7:
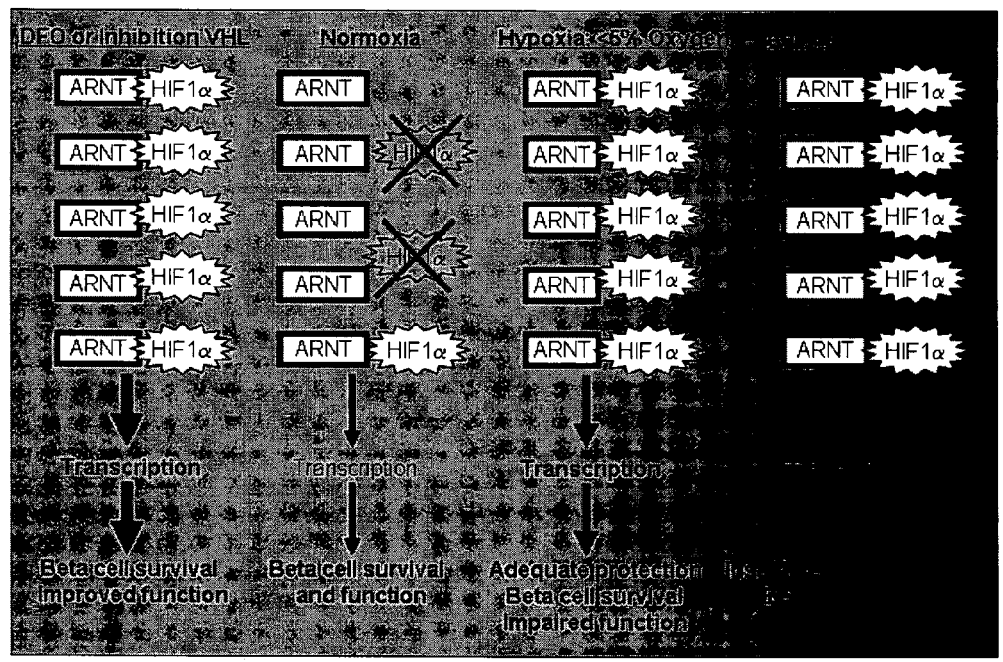

FIG. 7: DFO treatment improves outcome of minimal-mass human islet transplantation in mice. (A) Human islets from 3 different donors were transplanted into diabetic SCID mice either in an excess number (2000 IEQ per mouse), or in a minimal mass number (600 IEQ per mouse). The minimal mass islets were treated with control or DFO at 125 µmol/L for 2 hours prior to transplantation. As shown, large numbers of islets from each preparation were able to reverse diabetes in all recipients (n=3). As expected, 600 IEQ isolated from the same people cured diabetes in 0% (n=6). In contrast, 2 hours of culture with DFO improved outcome following transplantation of 600 IEQ to 75% (n=8). (B) Model of HIF-1α function in β-cells. DFO treatment increases HIF-1α by inhibiting its degradation, and has marked beneficial effects on β-cell function. Under normoxic conditions, HIF-1α is required for normal β-cell function, as loss by RNAi in cell culture or deletion in mice impairs GSIS. The pancreas is normally exposed to relative hypoxia (5-8% O2), and under these conditions, HIF-1α is particularly important for survival and maintenance of β-cell function. In the setting of anoxia, HIF-1α is not able to prevent β-cell demise.

KEY TO SEQUENCE LISTING

SEQ ID NO: 1=*Homo sapiens* HIF-1α protein isoform 1 [accession no. NP_001521]
SEQ ID NO: 2=*Homo sapiens* HIF-1α protein isoform 2 [accession no. NP_851397]
SEQ ID NO: 3=*Mus musculus* HIF-1α protein [accession no. NP_034561]
SEQ ID NO: 4=*Rattus norvegicus* HIF-1α protein [accession no. NP_077335]
SEQ ID NO: 5=*Homo sapiens* HIF-1α cDNA variant 1 [accession no. NM_001530]
SEQ ID NO: 6=*Homo sapiens* HIF-1α cDNA variant 2 [accession no. NM_181054]
SEQ ID NO: 7=*Mus musculus* HIF-1α cDNA [accession no. NM_010431]
SEQ ID NO: 8=*Rattus norvegicus* HIF-1α cDNA [accession no. NM_024359]
SEQ ID NO: 9=*Homo sapiens* VHL protein isoform 1 [accession no. NP_000542]
SEQ ID NO: 10=*Homo sapiens* VHL protein isoform 2 [accession no. NP_937799]
SEQ ID NO: 11=*Mus musculus* VHL protein [accession no. NP_033533]
SEQ ID NO: 12=*Rattus norvegicus* VHL protein [accession no. NP_434688]
SEQ ID NO: 13=*Homo sapiens* VHL cDNA variant 1 [accession no. NM_000551]
SEQ ID NO: 14=*Homo sapiens* VHL cDNA variant 2 [accession no. NM_198156]
SEQ ID NO: 15=*Mus musculus* VHL cDNA [accession no. NM_009507]
SEQ ID NO: 16=*Rattus norvegicus* VHL cDNA [accession no. NM_052801]
SEQ ID NO: 17=VHL siRNA
SEQ ID NO: 18=VHL siRNA
SEQ ID NO: 19=VHL siRNA
SEQ ID NO: 20=VHL siRNA
SEQ ID NO: 21=Identified peptide (matched amino acid sequence for HIF-1α)
SEQ ID NO: 22=Identified peptide (matched amino acid sequence for HIF-1α)
SEQ ID NO: 23=Identified peptide (matched amino acid sequence for HIF-1α)
SEQ ID NO: 24=Identified peptide (matched amino acid sequence for HIF-1α)
SEQ ID NO: 25=Identified peptide (matched amino acid sequence for HIF-2α)
SEQ ID NO: 26=Identified peptide (matched amino acid sequence for HIF-2α)

DETAILED DESCRIPTION OF THE PREFERRED EMBODIMENTS

General Techniques

Unless specifically defined otherwise, all technical and scientific terms used herein shall be taken to have the same meaning as commonly understood by one of ordinary skill in the art (for example, in cell culture, molecular genetics, immunology, immunohistochemistry, protein chemistry, and biochemistry).

Unless otherwise indicated, the recombinant protein, cell culture, and immunological techniques utilised in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

Diabetes-Related Disorders

The present invention provides a method for treating a subject having or at risk of a diabetes-related disorder.

By "treating", it is meant to ameliorate, inhibit, lessen, reverse, or prevent a diabetes-related disorder, or to delay onset of a diabetes-related disorder.

By "diabetes-related disorder" it is meant to include diabetes and any manifested symptoms of diabetes in any mammal, such as impaired glucose tolerance, gestational diabetes, insulin resistance, β-cell dysfunction, insulitis. Human forms include type 1 and type 2 diabetes, gestational diabetes and rare monogenic forms such as the maturity onset diabetes of the young syndromes.

By "at risk of" it is meant a subject not formally diagnosed with diabetes, but demonstrating a symptom in terms of insulin or glucose level, and susceptibility to diabetes or a related condition due to family history, genetic predisposition, or obesity in the case of type 2 diabetes, or has previously had diabetes or a related condition and is subject to risk of recurrence.

HIF-1α Polypeptides and Polynucleotides

As used herein "HIF-1" is characterised as a DNA-binding protein which binds to a region in the regulatory, preferably in the enhancer region, of a structural gene having the HIF-1 binding motif. Included among the structural genes which can be activated by HIF-1 are erythropoietin (EPO), vascular endothelial growth factor (VEGF), and glycolytic gene transcription in cells subjected to hypoxia.

HIF-1 is composed of subunits HIF-1α and an isoform of HIF-1β. In addition to having domains which allow for their mutual association in forming HIF-1, the α and β subunits of HIF-1 both contain DNA-binding domains. The α subunit is uniquely present in HIF-1, whereas the β subunit (ARNT) is a component of at least two other transcription factors.

The methods of the present invention involve increasing the level or stability of HIF-1α in pancreatic β-cells or insulin-sensitive tissues of the subject.

By "insulin-sensitive tissues" it is meant tissues that are responsive to insulin action (including the uptake of glucose) at a clinically-normal level.

In one embodiment, the methods of the invention involve administering to the subject a HIF-1α polypeptide or an active fragment thereof, or a polynucleotide encoding HIF-1α polypeptide or an active fragment thereof.

The HIF-1α polypeptide can be a substantially purified, or recombinant polypeptide. Preferably, the HIF-1α polypeptide comprises a sequence which shares at least 75% identity with a sequence as shown in any one of SEQ ID NOS: 1 to 4.

By "substantially purified polypeptide" or "purified" we mean a polypeptide that has been separated from one or more lipids, nucleic acids, other polypeptides, or other contaminating molecules with which it is associated in its native state. It is preferred that the substantially purified polypeptide is at least 60% free, more preferably at least 75% free, and more preferably at least 90% free from other components with which it is naturally associated.

The term "recombinant" in the context of a polypeptide refers to the polypeptide when produced by a cell, or in a cell-free expression system, in an altered amount or at an altered rate compared to its native state. In one embodiment, the cell is a cell that does not naturally produce the polypeptide. However, the cell may be a cell which comprises a non-endogenous gene that causes an altered, preferably increased, amount of the polypeptide to be produced. A recombinant polypeptide of the invention includes polypeptides which have not been separated from other components of the transgenic (recombinant) cell, or cell-free expression system, in which it is produced, and polypeptides produced in such cells or cell-free systems which are subsequently purified away from at least some other components.

The terms "polypeptide" and "protein" are generally used interchangeably and refer to a single polypeptide chain which may or may not be modified by addition of non-amino acid groups. It would be understood that such polypeptide chains may associate with other polypeptides or proteins or other molecules such as co-factors. The terms "proteins" and "polypeptides" as used herein also include variants, mutants, modifications, analogous and/or derivatives of the polypeptides of the invention as described herein.

The % identity of a polypeptide is determined by GAP (Needleman and Wunsch, 1970) analysis (GCG program) with a gap creation penalty=5, and a gap extension penalty=0.3. The query sequence is at least 25 amino acids in length, and the GAP analysis aligns the two sequences over a region of at least 25 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids. Even more preferably, the GAP analysis aligns the two sequences over their entire length.

As used herein a "biologically active fragment" is a portion of a polypeptide of the invention which maintains a defined activity of the full-length polypeptide, namely be able to promote glucose stimulated insulin secretion (GSIS) and cell survival. In one embodiment, the biologically active fragment contains one and preferably both of the transactivation domains of HIF-1α. By "transactivation domains of HIF-1α" it is meant the $NH_2$-terminal transactivation domain (amino acids 531-575) and the COOH-terminal transactivation domain (amino acids 786-826) of HIF-1α that interact with general transcription machinery to activate transcription from promoters of HIF-1α. target genes. Biologically active fragments can be any size as long as they maintain the defined activity. Preferably, biologically active fragments are at least 100, more preferably at least 200, and even more preferably at least 350 amino acids in length.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99% identical to the relevant nominated SEQ ID NO.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final polypeptide product possesses the desired characteristics.

Mutant (altered) polypeptides can be prepared using any technique known in the art. For example, a polynucleotide of the invention can be subjected to in vitro mutagenesis. Such in vitro mutagenesis techniques may include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the invention are subjected to DNA shuffling techniques as broadly described by Harayama (1998). Products derived from mutated/altered DNA can readily be screened using techniques described herein to determine if they are able to confer enhanced GSIS, and/or improved islet graft survival.

In designing amino acid sequence mutants, the location of the mutation site and the nature of the mutation will depend on characteristic(s) to be modified. The sites for mutation can be modified individually or in series, for example, by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as important for function. Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 1 under the heading of "exemplary substitutions".

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are polypeptides of the present invention which are differentially modified during or after synthesis, for example, by biotinylation, benzylation, glycosylation, acetylation, phosphorylation, amidation, derivatization by known protecting/blocking groups, proteolytic cleavage, linkage to an antibody molecule or other cellular ligand, etc. These modifications may serve to increase the stability and/or bioactivity of the polypeptide of the invention.

TABLE 1

Exemplary substitutions

| Original Residue | Exemplary Substitutions |
|---|---|
| Ala (A) | val; leu; ile; gly |
| Arg (R) | lys |
| Asn (N) | gln; his |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe; ala |

Polypeptides of the present invention can be produced in a variety of ways, including production and recovery of natural polypeptides, production and recovery of recombinant polypeptides, and chemical synthesis of the polypeptides. In one embodiment, an isolated polypeptide of the present invention is produced by culturing a cell capable of expressing the polypeptide under conditions effective to produce the polypeptide, and recovering the polypeptide. Effective culture conditions include, but are not limited to, effective media, bioreactor, temperature, pH and oxygen conditions that permit polypeptide production. An effective medium refers to any medium in which a cell is cultured to produce a polypeptide of the present invention. Such medium typically comprises an aqueous medium having assimilable carbon, nitrogen and phosphate sources, and appropriate salts, minerals, metals and other nutrients, such as vitamins. Cells can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

In another embodiment, the methods of the invention involve administration of a polynucleotide encoding HIF-1α or an active fragment thereof. The HIF-1α polynucleotide can be an isolated or exogenous polynucleotide. Preferably, the HIF-1α polynucleotide comprises a sequence which shares at least 75% identity with a sequence as shown in any one of SEQ ID NOS: 5 to 8.

By an "isolated polynucleotide", including DNA, RNA, or a combination of these, single or double stranded, in the sense or antisense orientation or a combination of both, dsRNA or otherwise, we mean a polynucleotide which is at least partially separated from the polynucleotide sequences with which it is associated or linked in its native state. Preferably, the isolated polynucleotide is at least 60% free, preferably at least 75% free, and most preferably at least 90% free from other components with which they are naturally associated. Furthermore, the term "polynucleotide" is used interchangeably herein with the term "nucleic acid".

The term "exogenous" in the context of a polynucleotide refers to the polynucleotide when present in a cell, or in a cell-free expression system, in an altered amount compared to its native state. In one embodiment, the cell is a cell that does not naturally comprise the polynucleotide. However, the cell may be a cell which comprises a non-endogenous polynucleotide resulting in an altered, preferably increased, amount of production of the encoded polypeptide. An exogenous polynucleotide of the invention includes polynucleotides which have not been separated from other components of the transgenic (recombinant) cell, or cell-free expression system, in which it is present, and polynucleotides produced in such cells or cell-free systems which are subsequently purified away from at least some other components.

The % identity of a polynucleotide is determined by GAP (Needleman and Wunsch, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides. Even more preferably, the GAP analysis aligns the two sequences over their entire length.

With regard to the defined polynucleotides, it will be appreciated that % identity figures higher than those provided above will encompass preferred embodiments. Thus, where applicable, in light of the minimum % identity figures, it is preferred that a polynucleotide of the invention comprises a sequence which is at least 75%, more preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

Administration of HIF-1α Polypeptides and Polynucleotides

In a preferred embodiment of the invention, an HIF-1α polypeptide or active fragment thereof is administered with a biologically acceptable carrier.

The phrase, "biologically acceptable carrier" refers to any diluent, excipient, additive, or solvent which is either pharmaceutically accepted for use in the mammal for which a composition is formulated.

Routes of administration of the polypeptide or active fragment thereof include but are not limited to parenteral (for example, intravenous, intradermal, intraperitoneal or subcutaneous), oral, inhalational (for example, intranasal), transdermal (for example, topical), transmucosal, and rectal administration.

In a further preferred embodiment of the invention, the HIF-1α polynucleotide is inserted into a recombinant expression vector for the purposes of administration to the subject.

The term "recombinant expression vector" refers to a plasmid, virus or other vehicle known in the art that has been manipulated by insertion or incorporation of the HIF-1α genetic sequences. Such expression vectors contain a promoter sequence which facilitates the efficient transcription in the host of the inserted genetic sequence. The expression vector typically contains an origin of replication, a promoter, as well as specific genes which allow phenotypic selection of the transformed cells.

In one embodiment, the viral vector is derived from adeno-associated virus (AAV) and comprises a constitutive or regulatable promoter capable of driving sufficient levels of expression of the HIF-1α-encoding DNA in the viral vector. Preferably, the viral vector comprises inverted terminal repeat sequences of AAV, such as those described in WO 93/24641. In a preferred embodiment, the viral vector comprises polynucleotide sequences of the pTR-UF5 plasmid. The pTR-UF5 plasmid is a modified version of the pTR$_{BS}$-UF/UF1/UF2/UFB series of plasmids (Zolotukiin et al., 1996; Klein et al., 1998).

Promoters useful with the subject invention include, for example, the cytomegalovirus immediate early promoter (CMV), the human elongation factor 1-α promoter (EF1), the small nuclear RNA promoters (U1a and U1b), α-myosin heavy chain promoter, Simian virus 40 promoter (SV40), Rous sarcoma virus promoter (RSV), Adenovirus major late promoter, β-actin promoter and hybrid regulatory element comprising a CMV enhancer/β-actin promoter. These promoters have been shown to be active in a wide range of mammalian cells.

The promoters are operably linked with heterologous DNA encoding HIF-1α. By "operably linked", it is intended that the promoter element is positioned relative to the coding sequence to be capable of effecting expression of the coding sequence.

Promoters particularly useful for expression of a protein in islet cells include, for example the insulin promoter (for example, the rat insulin promoter) and the PDX1/IPF1 promoter.

Also contemplated for use with the vectors of the present invention are inducible and cell type specific promoters. For example, Tet-inducible promoters (Clontech, Palo Alto, Calif.) and VP16-LexA promoters (Nettelbeck et al., 1998) can be used in the present invention.

The vectors can also include introns inserted into the polynucleotide sequence of the vector as a means for increasing expression of heterologous DNA encoding HIF-1α. For example, an intron can be inserted between a promoter sequence and the region coding for the protein of interest on the vector. Introns can also be inserted in the coding regions. Transcriptional enhancer elements which can function to increase levels of transcription from a given promoter can also be included in the vectors of the invention. Enhancers can generally be placed in either orientation, 3' or 5', with respect to promoter sequences. In addition to the natural enhancers, synthetic enhancers can be used in the present invention. For example, a synthetic enhancer randomly assembled from Spc5-12-derived elements including muscle-specific elements, serum response factor binding element (SRE), myocyte-specific enhancer factor-1 (MEF-1), myocyte-specific enhancer factor-2 (MEF-2), transcription enhancer factor-1 (TEF-1) and SP-1 (Li et al., 1999; Deshpande et al., 1997; Stewart et al., 1996; Mitchell and Tjian, 1989; Briggs et al., 1986; Pitluk et al., 1991) can be used in vectors of the invention.

The gene therapy methods of the invention can be performed by ex vivo or in vivo treatment of the patient's cells or tissues, preferably the patient's islet cells or pancreatic tissue. The vectors of the invention can be introduced into suitable cells, cell lines or tissue using methods known in the art. The viral particles and vectors can be introduced into cells or tissue in vitro or in vivo. Methods contemplated include transfection, transduction, injection and inhalation. For example, vectors can be introduced into cells using liposomes containing the subject vectors, by direct transfection with vectors alone, electroporation or by particle bombardment. In an exemplified embodiment, islet cells are infected in vivo by injection of viral particles comprising recombinant vector into pancreatic tissue of the subject.

The dosage of recombinant vector or the virus to be administered to the subject can be determined by the ordinarily skilled clinician based on various parameters such as mode of administration, duration of treatment, the disease state or condition involved, and the like. Typically, recombinant virus of the invention is administered in doses between $10^5$ and $10^{14}$ infectious units. The recombinant vectors and virus of the present invention can be prepared in formulations using methods and materials known in the art. Numerous formulations can be found in Remington's Pharmaceutical Sciences, $15^{th}$ Edition (1975).

Inhibitors of Proteins that Mediate Degradation of HIF-1α

In one embodiment, the methods of the invention involve administering to the subject an inhibitor of a protein that mediates degradation of HIF-1α.

In a preferred embodiment, the protein that mediates degradation of HIF-1α is a Von Hippel-Lindau protein (VHL). Preferably, the VHL protein has a sequence which shares at least 75% identity with a sequence as shown in any one of SEQ ID NO: 9 to 12.

In a further preferred embodiment, the inhibitor of a protein that mediates degradation of HIF-1α is selected from the group consisting of an antisense polynucleotide, ribozyme, PNA, interfering RNA, siRNA, microRNA or antibody. These inhibitors are described in detail below. In a preferred embodiment, the inhibitor targets the portion of the VHL protein that binds to the oxygen degradation domain of HIF-1α.

Antisense Polynucleotides

The term "antisense polynucleotide" shall be taken to mean a DNA or RNA, or combination thereof, molecule that is complementary to at least a portion of a specific mRNA molecule encoding a polypeptide of the invention and capable of interfering with a post-transcriptional event such as mRNA translation. The use of antisense methods is well known in the art (see for example, G. Hartmann and S. Endres, Manual of Antisense Methodology, Kluwer (1999)).

An antisense polynucleotide of the invention will hybridise to a target polynucleotide under physiological conditions. As used herein, the term "an antisense polynucleotide which hybridises under physiological conditions" means that the polynucleotide (which is fully or partially single stranded) is at least capable of forming a double stranded polynucleotide with mRNA encoding a protein, such as those encoding the VHL protein (the corresponding cDNA sequence of which is provided in any one of SEQ ID NO:13 to 16) under normal conditions in a cell, preferably a β-cell.

Antisense molecules may include sequences that correspond to the structural genes or for sequences that effect control over the gene expression or splicing event. For example, the antisense sequence may correspond to the targeted coding region of the genes of the invention, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences which may function to stabilise the molecule.

Catalytic Polynucleotides

The term "catalytic polynucleotide/nucleic acid" refers to a DNA molecule or DNA-containing molecule (also known in the art as a "deoxyribozyme") or an RNA or RNA-containing molecule (also known as a "ribozyme") which specifically recognises a distinct substrate and catalyses the chemical modification of this substrate. The nucleic acid bases in the catalytic nucleic acid can be bases A, C, G, T (and U for RNA). Typically, the catalytic nucleic acid contains an antisense sequence for specific recognition of a target nucleic acid, and a nucleic acid cleaving enzymatic activity (also referred to herein as the "catalytic domain"). The types of ribozymes that are particularly useful in this invention are the hammerhead ribozyme (Haseloff and Gerlach, 1988, Perriman et al. 1992) and the hairpin ribozyme (Zolotukiin et al., 1996; Klein et al., 1998; Shippy et al., 1999).

The ribozymes of this invention and DNA encoding the ribozymes can be chemically synthesised using methods well known in the art. The ribozymes can also be prepared from a DNA molecule (that upon transcription, yields an RNA molecule) operably linked to an RNA polymerase promoter, for example, the promoter for T7 RNA polymerase or SP6 RNA polymerase. Accordingly, also provided by this invention is a nucleic acid molecule, that is, DNA or cDNA, coding for a catalytic polynucleotide of the invention. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilise the ribozyme and make it resistant to RNase.

As with antisense polynucleotides described herein, catalytic polynucleotides of the invention should also be capable of "hybridising" a target nucleic acid molecule (for example an mRNA encoding a VHL polypeptide (the corresponding cDNA sequences of which is provided in any one of SEQ ID NO: 13 to 16): under "physiological conditions", namely those conditions within a cell (especially conditions in a β-cell).

RNA Interference

RNA interference (RNAi) is particularly useful for specifically inhibiting the production of a particular protein. Although not wishing to be limited by theory, Waterhouse et al. (1998) have provided a model for the mechanism by which dsRNA (duplex RNA) can be used to reduce protein production. This technology relies on the presence of dsRNA molecules that contain a sequence that is essentially identical to the mRNA of the gene of interest or part thereof, in this case an mRNA encoding a protein that mediates degradation of HIF-1α. Conveniently, the dsRNA can be produced from a single promoter in a recombinant vector or host cell, where the sense and anti-sense sequences are flanked by an unrelated sequence which enables the sense and anti-sense sequences to hybridise to form the dsRNA molecule with the unrelated sequence forming a loop structure. The design and production of suitable dsRNA molecules for the present invention is well within the capacity of a person skilled in the art, particularly considering Waterhouse et al. (1998), Smith et al. (2000), WO 99/32619, WO 99/53050, WO 99/49029, and WO 01/34815.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridise to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous mammalian system that destroys both the double stranded RNA and also the homologous RNA transcript from the target mammalian gene, efficiently reducing or eliminating the activity of the target gene.

The length of the sense and antisense sequences that hybridise should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilise the molecule. The RNA molecule may be expressed under the control of a RNA polymerase II or RNA polymerase III promoter. Examples of the latter include tRNA or snRNA promoters.

Preferred small interfering RNA ('siRNA") molecules comprise a nucleotide sequence that is identical to about 19-21 contiguous nucleotides of the target mRNA. Preferably, the siRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the mammal in which it is to be introduced, for example as determined by standard BLAST search. Examples of siRNA molecules that target VHL mRNA are provided in any one of SEQ ID NO:17 to 20.

microRNA

MicroRNA regulation is a clearly specialised branch of the RNA silencing pathway that evolved towards gene regulation, diverging from conventional RNAi/PTGS. MicroRNAs are a specific class of small RNAs that are encoded in gene-like elements organised in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression (see, for example, Millar and Waterhouse, 2005; Pasquinelli et al. 2005; Almeida and Allshire, 2005).

Polyclonal and Monoclonal Antibodies

If polyclonal antibodies are desired, a selected mammal (for example, mouse, rabbit, goat, horse, etc.) is immunised with an immunogenic polypeptide such as VHL (for example, as shown in any one of SEQ ID NO:9 to 12). Serum from the immunised animal is collected and treated according to known procedures. If serum containing polyclonal antibodies contains antibodies to other antigens, the polyclonal antibodies can be purified by immunoaffinity chromatography. Techniques for producing and processing polyclonal antisera are known in the art. In order that such antibodies may be made, the invention also provides peptides of the invention or fragments thereof haptenised to another peptide for use as immunogens in animals.

Monoclonal antibodies directed against a protein that mediates the degradation of HIF-1α can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced can be screened for various properties; that is, for isotype and epitope affinity.

An alternative technique involves screening phage display libraries where, for example the phage express scFv fragments on the surface of their coat with a large variety of complementarity determining regions (CDRs). This technique is well known in the art. For the purposes of this invention, the term "antibody", unless specified to the contrary, includes fragments of whole antibodies which retain their binding activity for a target antigen. Such fragments include Fv, F(ab') and F(ab')$_2$ fragments, as well as single chain antibodies (scFv). Furthermore, the antibodies and fragments thereof may be humanized antibodies, for example as described in EP-A-239400.

Chelating Agents

In one preferred embodiment of the invention, the level or stability of HIF-1α activity is increased by administering to the subject a chelating agent.

A "chelating agent" refers to a substance, compound, mixture, or formulation capable of having an affinity for iron, copper or other transition metal and which is capable of binding iron or copper or any other transition metal in vitro or in vivo. When used in this invention, the chelating agent is useful in chelating/binding ferrous iron or copper or other transition metal and/or decreasing oxidative stress by acting as a transition metal sequestrant and/or antioxidant.

In a preferred embodiment, the chelating agent is an iron chelator.

The iron chelator is preferably selected from the group consisting of desferrioxamine (DFO), ferrioxamine, trihydroxamic acid, CP94, EDTA, desferrioxamine hydroxamic acids, deferoxamine B (DFO) as the methanesulfonate salt, also known as desferrioxamine B mesylate (DFOM), desferal from Novartis (previously Ciba-Giegy), apoferritin, CDTA (trans-1,2-diaminocyclohexane-N,N,N',N'-tetraacetic acid), and DTPA (diethylenetriamine-N,N,N',N'',N''-penta-acetic acid) and cobaltous ions.

The chelating agent may be administered by any suitable route. Routes of administration of the chelating agent include intramuscular, parenteral (including intravenous), intraarterial, subcutaneous, oral, and nasal administration.

Preferably, the chelating agent is administered in at least one dose that is within the range 0.0001 to 1.0 mg.kg.

In a preferred embodiment, the iron chelator is desferrioxamine (DFO).

In a further preferred embodiment the DFO is administered intravenously, diluted in normal saline. Preferably, the dose is within the range 5 g to 10 g per person. Preferably the dose is administered once weekly.

EXAMPLES

Example 1

Materials and Methods

Human Pancreatic Islets

Human pancreatic islets were purified from seven normoglycemic subjects using the modified Ricordi method (Ricordi et al., 1988) as previously described (Gunton et al., 2005). The subjects are described in (Gunton et al., 2005), and were matched for age and body-mass-index. Gene expression was measured by real-time-PCR and was performed in a two-step reaction using the Invitrogen RT-for-PCR kit. The second step was performed in a fluorescent temperature cycler (ABI-Prism 7700 Sequence Detection System, Applied Biosystems) with LightCycler-RNA Master SYBR-Green-I (Roche, Mannheim, Germany) and specific primers for each of the genes (sequences available on request). Every plate included a control gene (TATA-box binding protein/TBP) for every subject. Results were analysed by unpaired t-test.

Islet Isolation from Mice

Pancreatic islets were isolated from mice aged 9-12 weeks, as previously described (Kulkarni et al., 1999; Gunton et al., 2005).

Affinity Purification, Mass Spectrometry and Co-Immunoprecipitation

ARNT2, HIF1α and HIF2α/EPAS1 antibodies were purchased from Novus Biologicals (Littleton, Colo.), AhR antibodies from Orbigen (San Diego, Calif.) and ARNT antibodies from BD Biosciences. Anti-mouse and anti-rabbit secondary antibodies were purchased from Santa Cruz (Santa Cruz, Calif.).

ARNT-affinity-purification was done by binding ARNT antibody (12 µg) to 1 ml of packed protein A/G beads in 5 ml columns. No-antibody columns were used for control samples. Columns were washed with 20 mls of PBST to remove unbound antibody. Min6 cells were grown to 80-90% confluence in 4 20 cm dishes per condition. They were washed twice in PBS and placed in serum free DMEM at 25 mM glucose for 4 hours. DFO treatment was applied at 125 µM for 4 hours to the appropriate plates, or an equal volume of vehicle to control plates. Cells were collected by scraping into LID cell lysis buffer with protease and phosphatase inhibitors as previously described (Gunton et al., 2003). After centrifugation, nuclei were disrupted by sonication. The cytoplasmic or nuclear extracts were applied to the columns as indicated, and the flow-through re-applied twice to obtain maximal binding. After this, the columns were washed twice with 20 mls of LID buffer followed by 2 washes with 20 mls of PBST. The bound proteins were eluted with reducing sample buffer.

The eluted proteins were size-separated by 10% SDS-PAGE followed by staining for proteins with Coomassie blue.

For mass spectrometry, gel slices were digested with 5 ng/ml sequencing grade modified trypsin (Promega, Madison, Wis.) in 25 mM ammonium bicarbonate containing 0.01% n-octylglucoside for 18 hrs at 37° C. Peptides were eluted from the gel slices with 80% acetonitrile, 1% formic acid. Tryptic digests were separated by capillary HPLC(C18, 75 mM i.d. Picofrit column, New Objective, Woburn, Mass.) using a flow rate of 100 nl/min over a 3 hour reverse phase gradient and analysed using a LTQ linear Ion Trap LC/MS'' system (Thermo Electron, San Jose, Calif.). Resultant MS/MS spectra were searched against the NCBI nr database using TurboSequest (BioWorks 3.1, Thermo Electron) with cross-correlation scores>1.5, 2.0 and 2.5 for charge states $U^{108}$, $u^{108}$ and $\mho$, respectively, >30% fragment ions, and Rsp<3. Proteins were identified with >2 unique peptide matches.

Co-immunoprecipitation studies were performed using 2 µg of the indicated antibody, overnight incubation with the indicated cell-lysate, washing, elution with reducing sample buffer, and separation by 10% SDS-PAGE. Proteins were detected with the indicated antibody followed by the appropriate HRP-conjugated secondary antibody and detection by enhanced chemiluminescence.

Measurement of Intracellular ATP Concentrations

ATP concentrations were measured in islets and in Min6 cells following exposure to low (1 mM) or high glucose (25 mM) for 30 minutes. At the 30 minute timepoint, cells were placed on ice, washed twice in ice-cold PBS and lysed and ATP was measured using a kit purchased from Roche, according to the manufacturer's instructions.

Small Interfering RNA (RNAi) Treatment of Min6 Cells and Insulin Release

Using Min6 cells, HIF-1α was decreased by 48 hours of treatment with small interfering RNA (siRNA/RNAi) "smartpool" (Dharmacon, Lafayette, Colo.), transfected using Lipofectamine 2000 (Invitrogen), according to the respective manufacturers' protocols. Scrambled-sequence RNAi was used as a control in all experiments. Glucose-stimulated insulin secretion (GSIS) was assessed in triplicate wells in 3 separate experiments, and corrected for total insulin content, which did not change in treated cells (data not shown).

In separate experiments, treated cells were lysed, and RNA isolated for real-time-PCR.

Generation of β-Cell-Specific HIF-1α Knockout Mice

β-cell-specific HIF-1α knockout mice (β-HIF-1α) were generated using the Cre-lox system. Mice with floxed HIF-1α as previously described (Tomita et al., 2003) were bred with mice expressing Cre under control of the Rat Insulin Promoter (RIP-Cre mice). The RIP-Cre-alone mice have normal glucose tolerance (data not shown).

Transplantation of Islets Isolated from β-HIF-1α Knockout Mice or Floxed-Controls Islets were isolated from mice as described above. Islets were transplanted into immunodeficient mice (SCID) which were rendered diabetic by injection of 80 mg/kg of Alloxan IV. Blood glucose was monitored in the recipient mice by tail-nick 3 times a week. At 28 days, nephrectomy was performed to exclude regeneration of endogenous β-cells in the recipient mice. The kidney was collected for fresh-frozen section as described above for pancreatic sections and the graft was examined following H&E staining.

Example 2

Expression of Hypoxia-Inducible Factor-1α (HIF-1α) is Decreased in Islets Isolated from People with Type 2 Diabetes The present inventors measured HIF-1α gene expression in human islets isolated from people with normal glucose tolerance or type 2 diabetes. The islet donors have been previously described (Gunton et al., 2005). The present inventors also measured expression of other bHLH-PAS family members, aryl hydrocarbon receptor (AhR) and HIF-2α. By real-time PCR, expression of HIF-1α, HIF-2α/EPAS1 and AhR were all clearly detected in human islets (FIG. 1A), as was ARNT. HIF-1α mRNA expression was decreased by 90% in islets from people with type 2 diabetes (FIG. 1A, p<0.001). As previously reported by the inventors (Gunton et al., 2005), there was also a 90% decrease in expression of ARNT. Expression of AhR was also significantly decreased (p<0.05) and there was no significant change in expression of HIF-2α.

Example 3

HIF-1α Expression is Decreased in Islets from β-Cell Specific ARNT Knockout Mice In isolated murine islets, expression of HIF-1α, HIF-2α, AhR and ARNT mRNAs were clearly detected. Interestingly, in β-cell specific ARNT knockout mice (white bars), as in type 2 diabetes islets which had decreased ARNT, HIF-1α expression was markedly decreased (FIG. 1B), suggesting a potential role for ARNT in the transcriptional regulation of HIF-1α at the mRNA level.

Example 4

HIF-1α has a Direct Protein-Protein Interaction with ARNT in Min6 Cells in the Basal State and Following Exposure to Hypoxia-Mimics To determine which bHLH-PAS transcription factors were bound to ARNT and thus were potentially transcriptionally active, the inventors used ARNT-affinity purification and mass spectrometry as described in materials and methods. From this, the inventors identified peptides which matched the amino acid sequences for HIF-1α (SIYEYYHALDSDHLTK (SEQ ID NO: 21), PPM*TCLVLICEPIPHPSNIEIPLDSK (SEQ ID NO: 22), TFLSRHSLDMK#FSYCDER (SEQ ID NO: 23) and TM*NIKSATWK (SEQ ID NO: 24)), and HIF-2α (ENLTLK#NGSGFGK (SEQ ID NO: 25) and M*RSAKDFGAR (SEQ ID NO: 26)) in the nuclear fractions of Min6 cells.

Of importance, the HIF-1α peptides were identified in both the basal state (Lane 3, FIG. 1C) and following treatment with the hypoxia-mimic desferrioxamine (DFO) (Lane 4, FIG. 1C), whereas HIF-2α was only identified following DFO treatment (Lane 4, FIG. 1C). This suggested that HIF-1α protein may escape degradation in Min6 cells without hypoxia or cytokine treatment, that is, in the basal state.

The inventors confirmed that HIF-1α was bound to ARNT in both the basal state and following DFO treatment by co-immunoprecipitation studies. Antibodies to HIF-1α, HIF-2α and AhR were able to precipitate ARNT from the Min6 lysates as shown in FIG. 1D. Reciprocally, antibodies to ARNT co-immunoprecipitated HIF-1α from the nuclear fraction of Min6 cells both in the basal state (Lane 3, FIG. 1E) and following stimulation of HIF-1α protein by treatment with DFO (Lane 4, FIG. 1E). In an analogous fashion, FIG. 1F shows that anti-ARNT antibodies also co-precipitated HIF-2α in the basal (Lane 3) and DFO-stimulated states (Lane 4), although with lower efficacy. In contrast, FIG. 1G shows that anti-ARNT antibodies did not co-precipitate detectable amounts of Ahr in Min6 cell lysates from either the nuclear or the cytoplasmic components, despite clearly detecting AhR protein by Western blot (data not shown).

Example 5

HIF-1α Protein is Detectable in Pancreas and Islets in the Basal State, and HIF-1α Protein is Decreased in the Islets of People with Type 2 Diabetes Since HIF-1α is tightly regulated at the protein level, the present inventors sought to investigate whether the HIF-1α protein was present in normal pancreas. Immunoprecipitation studies were performed from a range of mouse tissues as shown in FIG. 2. As shown in Lane 8, whole pancreas has readily detectable amounts of HIF-1α protein. Muscle has been previously reported to express significant amounts of HIF-1α protein, and this experiment reproduces that finding (Lane 4).

Example 6

HIF-1α Knockdown by RNA-Interference Severely Impairs Glucose-Stimulated Insulin Release in Min6 Cells To clarify the function/roles of HIF-1α, HIF-2α and AhR in β-cells, the present inventors used the murine insulinoma-derived β-cell line of Min6 cells, which maintain GSIS. Using RNA interference (RNAi), the present inventors knocked down expression of AhR, HIF-1α and HIF-2α individually and in combination. As shown in FIG. 3A, HIF-1α and AhR RNAi both achieved ~75% knockdown, and HIF-2α RNAi caused ~65% knockdown.

In FIG. 3B, the present inventors show that in control RNAi treated Min6 cells, intracellular ATP concentration increases by 40% following exposure to 25 mM glucose. However, in cells treated with HIF-1α RNAi, there was no increase in intracellular ATP. Consistent with these findings, FIG. 3C shows that decreasing HIF-1α caused a severe impairment in GSIS. Interestingly, HIF-1α RNAi did not impair KCl stimulated insulin release (data not shown), suggesting a specific glucose-sensing defect. Combining HIF-1α with HIF-2α RNAi to decrease expression of both genes did not further impair GSIS, but combination of HIF-1α, HIF-2α and AhR produced a defect in GSIS which did not differ significantly from that produced by ARNT RNAi, suggesting a small but significant role of AhR in β-cell function. This is consistent with the fact that 23% of AhR knockout mice develop glucose intolerance by 8 months of age (Fernandez-Salguero et al., 1997).

Example 7

HIF-1α RNA-Interference Impairs Gene Expression

Following treatment with HIF-1α RNAi, the present inventors measured expression of genes in the maturity onset diabetes of the young (MODY) family, insulin-signalling and glucose-uptake and glycolytic genes by real-time PCR. The present inventors found substantially decreased expression of 3 of the MODY genes: TCF1 (encoding hepatocyte nuclear factor (HNF)-1α), PDX1/IPF-1 and glucokinase (GK) (FIG. 3D). HNF4α also showed a trend towards decreased expression following HIF-1α knockdown (p<0.07). In the insulin signaling pathway, HIF-1α knockdown decreased insulin-receptor substrate (IRS)-2 mRNA (FIG. 3E). HIF-1α has been reported to regulate expression of glycolytic genes in other tissues, and consistent with this, FIG. 3F shows that decreasing HIF-1α caused markedly decreased expression of the glucose transporters GLUT1 and GLUT2 (data not shown), and several components of the glycolytic pathway including glucose-6-phosphoisomerase (G6PI), phosphofructokinase (PFK), aldolase and phosphoglucomutase (PGM) (all p<0.01).

Example 8

β-Cell Specific HIF-1α Knockout Mice (β-HIF-1α) are Glucose Intolerant with Failure of Glucose Stimulated Insulin Secretion Whole-body deletion of HIF-1α is embryonic lethal in mice (Hofer et al., 2002; Iyer et al., 1998; Kotch et al., 1999), so in order to study the role of HIF-1α in β-cell function in vivo, the present inventors generated β-cell HIF-1α knockout mice using the Cre-lox system, with Cre under control of the rat insulin promoter (RIP-Cre). The RIP-Cre mice have normal glucose tolerance and insulin release (data not shown). The mice were born in a normal Mendelian distribution, were of normal weight and size and were fertile.

On glucose tolerance testing (GTT), both female and male β-HIF-1α mice showed marked glucose intolerance (FIGS. 4A and 4B), both p<0.001 by ANOVA for repeated measures. By measuring GSIS, the present inventors found that the glucose intolerance is caused by failure of first-phase insulin secretion in both female (FIG. 4C) and male mice (FIG. 4D). The female mice display prolonged elevation in their glucose at 120 minutes into the GTT, and consistent with this, female mice also have slightly lower circulating insulin at 20 minutes into the GSIS, showing that second phase insulin release is also impaired in female mice (FIG. 4C).

Example 9

Islets from a Mice Show a Marked Right-Shift in Glucose Stimulated Insulin Release Islets were isolated from β-HIF-1α mice as described in Methods and Materials. FIG. 4E shows that there were no significant differences in total insulin content between knockout and floxed-control mice. However, FIG. 4F shows that islets from β-HIF-1α knockout mice had markedly impaired insulin secretion at glucose concentrations of 5 mM (p=0.016) and 11 mM (p=0.001). At 22 mM glucose, the difference was no longer statistically significant (p=0.116), suggesting a right-shift in GSIS.

Example 10

Islets with β-Cell Deletion of HIF-1α Show Primary-Non-Function with Failure of Glycemic Control Following Islet Transplantation Isolated human or rat islets exposed to 1% oxygen for 24 hours show central cell death, demonstrating that islets are sensitive to hypoxia (Giuliani et al., 2005). In order to investigate the role of HIF-1α in islet transplantation with relevance to the human model, the present inventors performed minimal-mass islet transplantation of islets isolated from β-HIF-1α knockout mice or their floxed controls into SCID mice which had been rendered diabetic by 70 mg/kg of Alloxan IV.

As shown in FIG. 5, β-HIF-1α knockout islets were less able to control glucose post-transplantation in this model, with average random glucose levels of 18.7±3.0 versus 7.3±1.9 mmol/L at day 28 post-transplantation.

Example 11

Increased HIF-1α Protein in Min6 Cells Improves Gene Expression and Glucose Stimulated Insulin Release Because HIF-1α has been associated with protection from apoptosis during carcinogenesis, the present investigators examined the effects of increasing HIF-1α upon β-cell function.

Min6 cells were treated with DFO at the doses indicated for 4 hours. As shown in FIG. 6A, DFO treatment did not increase expression of either of the housekeeping genes TATA-box binding protein (TBP) or transthyretin. There was a small but significant increase in HIF-1α expression at the highest dose of DFO treatment (FIG. 6B) again consistent with a possible auto-regulation of HIF-1. DFO treatment dose-dependently increased expression of mRNAs for Akt2 and GLUT1 (both p<0.001), GLUT2, HNF4α, and IRS2 (all p<0.01) and phosphoglucomutase (PGM) (p<0.05). Expression of HNF1α, HNF1β, and insulin receptor did not alter with DFO treatment (data not shown).

As expected, given the increases in expression of glucose transporters and glycolytic enzymes, DFO treatment increased ATP generation in Min6 cells (FIG. 6E).

In association with the improved gene expression and ATP generation, DFO treatment also caused a substantial increase in GSIS (FIG. 6D). The present inventors were interested to determine whether DFO was beneficial for function of human islets. Islets were isolated from people with normal glucose tolerance and treated with control media or media supplemented with DFO for 4 hours, and insulin release subsequently measured at low (5 mM) and high (11 mM) glucose concentrations. As FIG. 6D shows, insulin release was markedly increased in DFO treated samples.

Example 12

Induction of Hypoxia Inducible Factors with DFO but not with 5% Oxygen Pre-Treatment Significantly Improves Outcome of Islet Transplantation in Mice Islets were isolated from control mice and cultured with either control media or control media plus 125 μM DFO under normoxic conditions or in control media under hypoxic conditions (5% O2) for 2 hours before transplantation. All the islets from 1 donor mouse were transplanted into 1 recipient mouse which had been rendered diabetic (random glucose>22 mM) by streptozotocin treatment.

Transplant recipients were followed for 28 days, at which time nephrectomy was performed to confirm recurrence of diabetes.

In control treated islets, mean glucose after transplantation was 16.4 mM. In DFO treated islets, the average glucose was 11.4 mM (p=0.01) and in hypoxic treated islets was 15.5 mM (p=0.013 versus DFO treated and p=ns versus control treatment).

Example 13

Treatment with DFO for 4 Hours Pre-Transplant Improves Outcome of Minimal Mass Human Islet Transplantation Human pancreatic islets were isolated from normal glucose tolerant donors as previously described (Gunton et al., 2005). Islets were transplanted under the left kidney capsule of SCID mice which had been rendered diabetic by injection of Alloxan at 95 mg/kg intravenously. Islets were transplanted in adequate mass (2000 IEQ per mouse), or minimal mass (600 IEQ per mouse). In each of the islet isolations, 2000 control-treated IEQ per mouse was adequate to cure diabetes. As expected, 600 control-treated IEQ per mouse was not adequate to control glucose at day 28 post-transplant in any mouse. Treatment with DFO at 125 µM for 4 hours pre-transplantation increased the success rate following transplant of 600 IEQ from 0% to 75%, p<0.00001 by Chi-Square.

REFERENCES

Almeida and Allshire (2005), TRENDS Cell Biol., 15:251-258.
Briggs et al. (1986), Science, 234:47-52.
Cetkovic et al. (1994), Cytokines, 6(4):399-406.
Deshpande et al. (1997), J. Biol. Chem., 272(16):10664-10668.
Fernandez-Salguero et al. (1997) Vet. Pathol., 34:605-614.
Giuliani et al. (2005), Cell Transplant., 14:67-76.
Gunton et al. (2003), J. Clin. Endocrinol. Metab., 88:1323-1332.
Gunton et al. (2005), Cell, 122:337-349.
Harayama (1998), Trends Biotechnol., 16: 76-82.
Haseloff and Gerlach (1988), Nature, 334:585-591.
Hofer et al. (2002), Pflugers Arch, 443:503-507.
Iyer et al. (1998), Genes Dev., 12:149-162.
Klein et al. (1998), Exp. Neurol., 150:183-194.
Kotch et al. (1999), Dev. Biol., 209:254-267.
Kulkarni et al. (1999), Cell, 96:329-339.
Li et al. (1999), Nat. Biotechnol., 17(3):241-245.
Mandrup-Poulsen (1996), Diabetologia, 39:1005-1029.
Millar and Waterhouse (2005), Funct. Integr. Genomics, 5:129-135.
Mitchell and Tjian (1989), Science, 245:371-378.
Needleman and Wunsch (1970), J. Mol. Biol., 48:443-453.
Nettelbeck et al. (1998), Gene Ther., 5(12)1656-1664.
Pasquinelli et al. (2005), Curr. Opin. Genet. Develop., 15:200-205.
Perriman et al. (1992), Gene, 113:157-163.
Pitluk et al. (1991), J. Virol., 65:6661-6670.
Ricordi et al. (1988), Diabetes, 37:413-420.
Shippy et al. (1999), Mol. Biotech., 12:117-129.
Smith et al. (2000), Nature, 407:319-320.
Stewart et al. (1996), Genomics, 37(1):68-76.
Tomita et al. (2003), Mol. Cell. Biol., 23(19):6739-6749.
Waterhouse et al. (1998), Proc. Natl. Acad. Sci. USA, 95:13959-13964.
Zolotukiin et al. (1996), J. Virol., 70(7):4646-4654.

The invention claimed is:

1. A method of transplanting pancreatic islet cells in a subject, the method comprising:
   (i) administering islet cells to the subject; and
   (ii) increasing the level or activity of Hypoxia Induced Factor 1α (HIF-1α) in the islet cells by contacting the islet cells with an effective amount of an inhibitor of a protein that decreases the level or activity of HIF-1α wherein the inhibitor is a chelating agent.

2. The method of claim 1, wherein the level or activity of HIF-1α is increased in the islet cells before transplantation.

3. The method of claim 1, wherein the level or activity of HIF-1α is increased in the islet cells after transplantation.

4. The method of claim 1, wherein the protein that decreases the level or activity of HIF-1α is a Von Hippel-Lindau protein (VHL).

5. The method of claim 1, wherein the inhibitor is an agent that promotes the dissociation of HIF-1α and the protein that decreases the level or activity of HIF-1α.

6. The method of claim 1, wherein the chelating agent is selected from the group consisting of desferrioxamine (DFO), ferrioxamine, trihydroxamic acid, CP94, EDTA, desferrioxamine hydroxamic acids, deferoxamine B (DFO) as the methanesulfonate salt, also known as desferrioxamine B mesylate (DFOM), desferal from Novartis (previously Ciba-Giegy), apoferritin, CDTA (trans-1,2-diaminocyclohexane-N,N,N',N'tetraaceticacid), and DTPA (diethylenetriamine-N,N,N',N",N"-penta-acetic acid) and cobaltous ions.

7. The method of claim 6, wherein the chelating agent is desferrioxamine (DFO).

8. The method of claim 1, wherein the subject is human.

9. A method for the treatment of a diabetes-related disorder, comprising the method of transplantation according to claim 1.

10. The method of claim 9, wherein the diabetes-related disorder is type 1 diabetes.

11. The method of claim 1, wherein the inhibitor of a protein that decreases the level or activity of HIF-1α is administered to the subject.

12. The method of claim 1, wherein the chelating agent is an iron chelating agent.

* * * * *

SEQUENCE LISTING

<160> NUMBER OF SEQ ID NOS: 26

<210> SEQ ID NO 1
<211> LENGTH: 826
<212> TYPE: PRT
<213> ORGANISM: Homo sapiens
<220> FEATURE:
<223> OTHER INFORMATION: HIF-1a protein isoform 1

<400> SEQUENCE: 1

```
Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
        50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125
```

-continued

```
Gly His Ser Val Phe Asp Phe Thr His Pro Cys Asp His Glu Glu Met
            130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
                195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
    275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
    355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
    435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
    515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560
```

```
Met Leu Ala Pro Tyr Ile Pro Met Asp Asp Phe Gln Leu Arg Ser
                565                 570                 575

Phe Asp Gln Leu Ser Pro Leu Glu Ser Ser Ala Ser Pro Glu Ser
            580                 585                 590

Ala Ser Pro Gln Ser Thr Val Thr Val Phe Gln Gln Thr Gln Ile Gln
            595                 600                 605

Glu Pro Thr Ala Asn Ala Thr Thr Thr Thr Ala Thr Thr Asp Glu Leu
    610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                645                 650                 655

Ser Pro Tyr Arg Asp Thr Gln Ser Arg Thr Ala Ser Pro Asn Arg Ala
            660                 665                 670

Gly Lys Gly Val Ile Glu Gln Thr Glu Lys Ser His Pro Arg Ser Pro
            675                 680                 685

Asn Val Leu Ser Val Ala Leu Ser Gln Arg Thr Thr Val Pro Glu Glu
    690                 695                 700

Glu Leu Asn Pro Lys Ile Leu Ala Leu Gln Asn Ala Gln Arg Lys Arg
705                 710                 715                 720

Lys Met Glu His Asp Gly Ser Leu Phe Gln Ala Val Gly Ile Gly Thr
                725                 730                 735

Leu Leu Gln Gln Pro Asp Asp His Ala Ala Thr Thr Ser Leu Ser Trp
            740                 745                 750

Lys Arg Val Lys Gly Cys Lys Ser Ser Glu Gln Asn Gly Met Glu Gln
            755                 760                 765

Lys Thr Ile Ile Leu Ile Pro Ser Asp Leu Ala Cys Arg Leu Leu Gly
    770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 2
<211> LENGTH: 735
<212> TYPE: PRT
<213> ORGANISM: Homo sapiens
<220> FEATURE:
<223> OTHER INFORMATION: HIF-1a protein isoform 2

<400> SEQUENCE: 2

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
                20                  25                  30

Glu Ser Glu Val Phe Tyr Glu Leu Ala His Gln Leu Pro Leu Pro His
            35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95
```

```
Asp Gly Phe Val Met Val Leu Thr Asp Asp Gly Asp Met Ile Tyr Ile
                100                 105                 110

Ser Asp Asn Val Asn Lys Tyr Met Gly Leu Thr Gln Phe Glu Leu Thr
                115                 120                 125

Gly His Ser Val Phe Asp Phe Thr His Pro Cys Asp His Glu Glu Met
            130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                    165                 170                 175

Ser Arg Gly Arg Thr Met Asn Ile Lys Ser Ala Thr Trp Lys Val Leu
                180                 185                 190

His Cys Thr Gly His Ile His Val Tyr Asp Thr Asn Ser Asn Gln Pro
            195                 200                 205

Gln Cys Gly Tyr Lys Lys Pro Pro Met Thr Cys Leu Val Leu Ile Cys
        210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
                260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525
```

```
Asn Glu Phe Lys Leu Glu Leu Val Glu Lys Leu Phe Ala Glu Asp Thr
            530                 535                 540
Glu Ala Lys Asn Pro Phe Ser Thr Gln Asp Thr Asp Leu Asp Leu Glu
545                 550                 555                 560
Met Leu Ala Pro Tyr Ile Pro Met Asp Asp Asp Phe Gln Leu Arg Ser
                565                 570                 575
Phe Asp Gln Leu Ser Pro Leu Glu Ser Ser Ser Ala Ser Pro Glu Ser
            580                 585                 590
Ala Ser Pro Gln Ser Thr Val Thr Val Phe Gln Gln Thr Gln Ile Gln
            595                 600                 605
Glu Pro Thr Ala Asn Ala Thr Thr Thr Thr Ala Thr Thr Asp Glu Leu
            610                 615                 620
Lys Thr Val Thr Lys Asp Arg Met Glu Asp Ile Lys Ile Leu Ile Ala
625                 630                 635                 640
Ser Pro Ser Pro Thr His Ile His Lys Glu Thr Thr Ser Ala Thr Ser
                645                 650                 655
Ser Pro Tyr Arg Asp Thr Gln Ser Arg Thr Ala Ser Pro Asn Arg Ala
                660                 665                 670
Gly Lys Gly Val Ile Glu Gln Thr Glu Lys Ser His Pro Arg Ser Pro
            675                 680                 685
Asn Val Leu Ser Val Ala Leu Ser Gln Arg Thr Thr Val Pro Glu Glu
690                 695                 700
Glu Leu Asn Pro Lys Ile Leu Ala Leu Gln Asn Ala Gln Arg Lys Arg
705                 710                 715                 720
Lys Met Glu His Asp Gly Ser Leu Phe Gln Ala Val Gly Ile Ile
                725                 730                 735

<210> SEQ ID NO 3
<211> LENGTH: 836
<212> TYPE: PRT
<213> ORGANISM: Mus musculus
<220> FEATURE:
<223> OTHER INFORMATION: HIF-1a protein

<400> SEQUENCE: 3

Met Glu Gly Ala Gly Gly Glu Asn Glu Lys Lys Lys Met Ser Ser Glu
1               5                   10                  15
Arg Arg Lys Glu Lys Ser Arg Asp Ala Ala Arg Ser Arg Arg Ser Lys
                20                  25                  30
Glu Ser Glu Val Phe Tyr Glu Leu Ala His Gln Leu Pro Leu Pro His
            35                  40                  45
Asn Val Ser Ser His Leu Asp Lys Ala Ser Val Met Arg Leu Thr Ile
            50                  55                  60
Ser Tyr Leu Arg Val Arg Lys Leu Leu Asp Ala Gly Gly Leu Asp Ser
65                  70                  75                  80
Glu Asp Glu Met Lys Ala Gln Met Asp Cys Phe Tyr Leu Lys Ala Leu
                85                  90                  95
Asp Gly Phe Val Met Val Leu Thr Asp Asp Gly Asp Met Val Tyr Ile
                100                 105                 110
Ser Asp Asn Val Asn Lys Tyr Met Gly Leu Thr Gln Phe Glu Leu Thr
            115                 120                 125
Gly His Ser Val Phe Asp Phe Thr His Pro Cys Asp His Glu Glu Met
            130                 135                 140
Arg Glu Met Leu Thr His Arg Asn Gly Pro Val Arg Lys Gly Lys Glu
145                 150                 155                 160
```

-continued

```
Leu Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Ser Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Cys Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asp
                405                 410                 415

Asp Thr Glu Thr Glu Asp Gln Gln Leu Glu Asp Val Pro Leu Tyr Asn
            420                 425                 430

Asp Val Met Phe Pro Ser Ser Asn Glu Lys Leu Asn Ile Asn Leu Ala
        435                 440                 445

Met Ser Pro Leu Pro Ser Ser Glu Thr Pro Lys Pro Leu Arg Ser Ser
    450                 455                 460

Ala Asp Pro Ala Leu Asn Gln Glu Val Ala Leu Lys Leu Glu Ser Ser
465                 470                 475                 480

Pro Glu Ser Leu Gly Leu Ser Phe Thr Met Pro Gln Ile Gln Asp Gln
                485                 490                 495

Pro Ala Ser Pro Ser Asp Gly Ser Thr Arg Gln Ser Ser Pro Glu Arg
            500                 505                 510

Leu Leu Gln Glu Asn Val Asn Thr Pro Asn Phe Ser Gln Pro Asn Ser
        515                 520                 525

Pro Ser Glu Tyr Cys Phe Asp Val Asp Ser Asp Met Val Asn Val Phe
    530                 535                 540

Lys Leu Glu Leu Val Glu Lys Leu Phe Ala Glu Asp Thr Glu Ala Lys
545                 550                 555                 560

Asn Pro Phe Ser Thr Gln Asp Thr Asp Leu Asp Leu Glu Met Leu Ala
                565                 570                 575

Pro Tyr Ile Pro Met Asp Asp Asp Phe Gln Leu Arg Ser Phe Asp Gln
            580                 585                 590
```

-continued

```
Leu Ser Pro Leu Glu Ser Asn Ser Pro Ser Pro Pro Ser Met Ser Thr
            595                 600                 605

Val Thr Gly Phe Gln Gln Thr Gln Leu Gln Lys Pro Thr Ile Thr Ala
        610                 615                 620

Thr Ala Thr Thr Thr Ala Thr Thr Asp Glu Ser Lys Thr Glu Thr Lys
625                 630                 635                 640

Asp Asn Lys Glu Asp Ile Lys Ile Leu Ile Ala Ser Pro Ser Ser Thr
                645                 650                 655

Gln Val Pro Gln Glu Thr Thr Thr Ala Lys Ala Ser Ala Tyr Ser Gly
            660                 665                 670

Thr His Ser Arg Thr Ala Ser Pro Asp Arg Ala Gly Lys Arg Val Ile
        675                 680                 685

Glu Gln Thr Asp Lys Ala His Pro Arg Ser Leu Lys Leu Ser Ala Thr
        690                 695                 700

Leu Asn Gln Arg Asn Thr Val Pro Glu Glu Leu Asn Pro Lys Thr
705                 710                 715                 720

Ile Ala Ser Gln Asn Ala Gln Arg Lys Arg Lys Met Glu His Asp Gly
                725                 730                 735

Ser Leu Phe Gln Ala Ala Gly Ile Gly Thr Leu Leu Gln Gln Pro Gly
            740                 745                 750

Asp Cys Ala Pro Thr Met Ser Leu Ser Trp Lys Arg Val Lys Gly Phe
        755                 760                 765

Ile Ser Ser Glu Gln Asn Gly Thr Glu Gln Lys Thr Ile Ile Leu Ile
770                 775                 780

Pro Ser Asp Leu Ala Cys Arg Leu Leu Gly Gln Ser Met Asp Glu Ser
785                 790                 795                 800

Gly Leu Pro Gln Leu Thr Ser Tyr Asp Cys Glu Val Asn Ala Pro Ile
            805                 810                 815

Gln Gly Ser Arg Asn Leu Leu Gln Gly Glu Glu Leu Leu Arg Ala Leu
        820                 825                 830

Asp Gln Val Asn
        835

<210> SEQ ID NO 4
<211> LENGTH: 823
<212> TYPE: PRT
<213> ORGANISM: Rattus norvegicus
<220> FEATURE:
<223> OTHER INFORMATION: HIF-1a protein

<400> SEQUENCE: 4

Met Glu Gly Ala Gly Gly Glu Asn Glu Lys Lys Asn Arg Met Ser Ser
1               5                   10                  15

Glu Arg Arg Lys Glu Lys Ser Arg Asp Ala Ala Arg Ser Arg Arg Ser
            20                  25                  30

Lys Glu Ser Glu Val Phe Tyr Glu Leu Ala His Gln Leu Pro Leu Pro
        35                  40                  45

His Asn Val Ser Ser His Leu Asp Lys Ala Ser Val Met Arg Leu Thr
    50                  55                  60

Ile Ser Tyr Leu Arg Val Arg Lys Leu Leu Gly Ala Gly Asp Leu Asp
65                  70                  75                  80

Ile Glu Asp Glu Met Lys Ala Gln Met Asn Cys Phe Tyr Leu Lys Ala
                85                  90                  95

Leu Asp Gly Phe Val Met Val Leu Thr Asp Asp Gly Asp Met Ile Tyr
            100                 105                 110
```

```
Ile Ser Asp Asn Val Asn Lys Tyr Met Gly Leu Thr Gln Phe Glu Leu
        115                 120                 125

Thr Gly His Ser Val Phe Asp Phe Thr His Pro Cys Asp His Glu Glu
        130                 135                 140

Met Arg Glu Met Leu Thr His Arg Asn Gly Pro Val Arg Lys Gly Lys
145                 150                 155                 160

Glu Gln Asn Thr Gln Arg Ser Phe Phe Leu Arg Met Lys Cys Thr Leu
                165                 170                 175

Thr Ser Arg Gly Arg Thr Met Asn Ile Lys Ser Ala Thr Trp Lys Val
            180                 185                 190

Leu His Cys Thr Gly His Ile His Val Tyr Asp Thr Ser Ser Asn Gln
        195                 200                 205

Pro Gln Cys Gly Tyr Lys Lys Pro Pro Met Thr Cys Leu Val Leu Ile
    210                 215                 220

Cys Glu Pro Ile Pro His Pro Ser Asn Ile Glu Ile Pro Leu Asp Ser
225                 230                 235                 240

Lys Thr Phe Leu Ser Arg His Ser Leu Asp Met Lys Phe Ser Tyr Cys
                245                 250                 255

Asp Glu Arg Ile Thr Glu Leu Met Gly Tyr Glu Pro Glu Glu Leu Leu
            260                 265                 270

Gly Arg Ser Ile Tyr Glu Tyr Tyr His Ala Leu Asp Ser Asp His Leu
        275                 280                 285

Thr Lys Thr His His Asp Met Phe Thr Lys Gly Gln Val Thr Thr Gly
    290                 295                 300

Gln Tyr Arg Met Leu Ala Lys Arg Gly Gly Tyr Val Trp Val Glu Thr
305                 310                 315                 320

Gln Ala Thr Val Ile Tyr Asn Thr Lys Asn Ser Gln Pro Gln Cys Ile
                325                 330                 335

Val Cys Val Asn Tyr Val Val Ser Gly Ile Ile Gln His Asp Leu Ile
            340                 345                 350

Phe Ser Leu Gln Gln Thr Glu Ser Val Leu Lys Pro Val Glu Ser Ser
        355                 360                 365

Asp Met Lys Met Thr Gln Leu Phe Thr Lys Val Glu Ser Glu Asp Thr
    370                 375                 380

Ser Cys Leu Phe Asp Lys Leu Lys Lys Glu Pro Asp Ala Leu Thr Leu
385                 390                 395                 400

Leu Ala Pro Ala Ala Gly Asp Thr Ile Ile Ser Leu Asp Phe Gly Ser
                405                 410                 415

Asp Asp Thr Glu Thr Glu Asp Gln Gln Leu Glu Asp Val Pro Leu Tyr
            420                 425                 430

Asn Asp Val Met Phe Pro Ser Ser Asn Glu Lys Leu Asn Ile Asn Leu
        435                 440                 445

Ala Met Ser Pro Leu Pro Ala Ser Glu Thr Pro Lys Pro Leu Arg Ser
    450                 455                 460

Ser Ala Asp Pro Ala Leu Asn Gln Glu Val Ala Leu Lys Leu Glu Ser
465                 470                 475                 480

Ser Pro Glu Ser Leu Gly Leu Ser Phe Thr Met Pro Gln Ile Gln Asp
                485                 490                 495

Gln Pro Ala Ser Pro Ser Asp Gly Ser Thr Arg Gln Ser Ser Pro Glu
            500                 505                 510

Pro Asn Ser Pro Ser Glu Tyr Cys Phe Asp Val Asp Ser Asp Met Val
        515                 520                 525

Asn Val Phe Lys Leu Glu Leu Val Glu Lys Leu Phe Ala Glu Asp Thr
    530                 535                 540
```

```
Glu Ala Lys Asn Pro Phe Ser Ala Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Asn Ser Pro Ser Pro Pro Ser
            580                 585                 590

Val Ser Thr Val Thr Gly Phe Gln Gln Thr Gln Leu Gln Lys Pro Thr
        595                 600                 605

Ile Thr Val Thr Ala Thr Ala Thr Ala Thr Asp Glu Ser Lys Ala
    610                 615                 620

Val Thr Lys Asp Asn Ile Glu Asp Ile Lys Ile Leu Ile Ala Ser Pro
625                 630                 635                 640

Pro Ser Thr Gln Val Pro Gln Glu Met Thr Thr Ala Lys Ala Ser Ala
                645                 650                 655

Tyr Ser Gly Thr His Ser Arg Thr Ala Ser Pro Asp Arg Ala Gly Lys
                660                 665                 670

Arg Val Ile Glu Lys Thr Asp Lys Ala His Pro Arg Ser Leu Asn Leu
            675                 680                 685

Ser Val Thr Leu Asn Gln Arg Asn Thr Val Pro Glu Glu Leu Asn
        690                 695                 700

Pro Lys Thr Ile Ala Leu Gln Asn Ala Gln Arg Lys Arg Lys Met Glu
705                 710                 715                 720

His Asp Gly Ser Leu Phe Gln Ala Ala Gly Ile Gly Thr Leu Leu Gln
                725                 730                 735

Gln Pro Gly Asp Arg Ala Pro Thr Met Ser Leu Ser Trp Lys Arg Val
            740                 745                 750

Lys Gly Tyr Ile Ser Ser Glu Gln Asp Gly Met Glu Gln Lys Thr Ile
        755                 760                 765

Phe Leu Ile Pro Ser Asp Leu Ala Cys Arg Leu Leu Gly Gln Ser Met
    770                 775                 780

Asp Glu Ser Gly Leu Pro Gln Leu Thr Ser Tyr Asp Cys Glu Val Asn
785                 790                 795                 800

Ala Pro Ile Gln Gly Ser Arg Asn Leu Leu Gln Gly Glu Glu Leu Leu
                805                 810                 815

Arg Ala Leu Asp Gln Val Asn
            820

<210> SEQ ID NO 5
<211> LENGTH: 3958
<212> TYPE: DNA
<213> ORGANISM: Homo sapiens
<220> FEATURE:
<223> OTHER INFORMATION: HIF-1a cDNA variant 1

<400> SEQUENCE: 5
gtgctgcctc gtctgagggg acaggaggat caccctcttc gtcgcttcgg ccagtgtgtc      60
gggctgggcc ctgacaagcc acctgaggag aggctcggag ccgggcccgg acccccggcga    120 ttgccgcccg cttctctcta gtctcacgag gggtttcccg cctcgcaccc ccacctctgg    180
acttgccttt ccttctcttc tccgcgtgtg gagggagcca gcgcttaggc cggagcgagc    240
ctggggggcc cccgccgtga agacatcgcg ggaccgatt caccatggag gcgccggcg     300 gcgcgaacga caagaaaaag ataagttctg aacgtcgaaa agaaaagtct cgagatgcag    360
ccagatctcg gcgaagtaaa gaatctgaag tttttatga gcttgctcat cagttgccac    420
ttccacataa tgtgagttcg catcttgata aggcctctgt gatgaggctt accatcagct    480
```

-continued

```
atttgcgtgt gaggaaactt ctggatgctg gtgatttgga tattgaagat gacatgaaag   540
cacagatgaa ttgcttttat ttgaaagcct tggatggttt tgttatggtt ctcacagatg   600
atggtgacat gatttacatt tctgataatg tgaacaaata catgggatta actcagtttg   660
aactaactgg acacagtgtg tttgatttta ctcatccatg tgaccatgag gaaatgagag   720
aaatgcttac acacagaaat ggccttgtga aaaagggtaa agaacaaaac acacagcgaa   780
gcttttttct cagaatgaag tgtaccctaa ctagccgagg aagaactatg aacataaagt   840
ctgcaacatg gaaggtattg cactgcacag gccacattca cgtatatgat accaacagta   900
accaacctca gtgtgggtat aagaaaccac ctatgacctg cttggtgctg atttgtgaac   960
ccattcctca cccatcaaat attgaaattc ctttagatag caagactttc ctcagtcgac  1020
acagcctgga tatgaaattt tcttattgtg atgaaagaat taccgaattg atgggatatg  1080
agccagaaga actttaggc cgctcaattt atgaatatta tcatgctttg gactctgatc  1140
atctgaccaa aactcatcat gatatgttta ctaaaggaca agtcaccaca ggacagtaca  1200
ggatgcttgc caaagaggt ggatatgtct gggttgaaac tcaagcaact gtcatatata  1260
acaccaagaa ttctcaacca cagtgcattg tatgtgtgaa ttacgttgtg agtggtatta  1320
ttcagcacga cttgattttc tcccttcaac aaacagaatg tgtccttaaa ccggttgaat  1380
cttcagatat gaaaatgact cagctattca ccaaagttga atcagaagat acaagtagcc  1440
tctttgacaa acttaagaag gaacctgatg ctttaacttt gctggcccca gccgctggag  1500
acacaatcat atctttagat tttggcagca acgacacaga aactgatgac cagcaacttg  1560
aggaagtacc attatataat gatgtaatgc tcccctcacc caacgaaaaa ttacagaata  1620
taaatttggc aatgtctcca ttacccaccg ctgaaacgcc aaagccactt cgaagtagtg  1680
ctgaccctgc actcaatcaa gaagttgcat taaaattaga accaaatcca gagtcactgg  1740
aactttcttt taccatgccc cagattcagg atcagacacc tagtccttcc gatggaagca  1800
ctagacaaag ttcacctgag cctaatagtc ccagtgaata ttgtttttat gtggatagtg  1860
atatggtcaa tgaattcaag ttggaattgg tagaaaaact ttttgctgaa gacacagaag  1920
caaagaaccc atttttctact caggacacag atttagactt ggagatgtta gctccctata  1980
tcccaatgga tgatgacttc cagttacgtt ccttcgatca gttgtcacca ttagaaagca  2040
gttccgcaag ccctgaaagc gcaagtcctc aaagcacagt tacagtattc cagcagactc  2100
aaatacaaga acctactgct aatgccacca ctaccactgc caccactgat gaattaaaaa  2160
cagtgacaaa agaccgtatg gaagacatta aaatattgat tgcatctcca tctcctaccc  2220
acatacataa agaaactact agtgccacat catcaccata tagagatact caaagtcgga  2280
cagcctcacc aaacagagca ggaaaaggag tcatagaaca gacagaaaaa tctcatccaa  2340
gaagccctaa cgtgttatct gtcgctttga gtcaaagaac tacagttcct gaggaagaac  2400
taaatccaaa gatactagct ttgcagaatg ctcagagaaa gcgaaaaatg gaacatgatg  2460
gttcactttt tcaagcagta ggaattggaa cattattaca gcagccagac gatcatgcag  2520
ctactacatc actttcttgg aaacgtgtaa aaggatgcaa atctagtgaa cagaatggaa  2580
tggagcaaaa gacaattatt ttaataccct ctgatttagc atgtagactg ctggggcaat  2640
caatggatga aagtggatta ccacagctga ccagttatga ttgtgaagtt aatgctccta  2700
tacaaggcag cagaaaccta ctgcagggtg aagaattact cagagctttg gatcaagtta  2760
actgagcttt tcttaatttt cattcctttt tttggacact ggtggctcac tacctaaagc  2820 agtctatttta tattttctac atctaatttt agaagcctgg ctacaatact gcacaaactt  2880
```

```
ggttagttca attttttgatc cccttttctac ttaatttaca ttaatgctct ttttagtat    2940 gttctttaat gctggatcac agacagctca ttttctcagt tttttggtat ttaaaccatt    3000
gcattgcagt agcatcattt taaaaaatgc acctttttat ttatttattt ttggctaggg    3060
agtttatccc tttttcgaat tatttttaag aagatgccaa tataatttt gtaagaaggc     3120 agtaaccttt catcatgatc ataggcagtt gaaaaatttt tacacctttt tttcacatt     3180 ttacataaat aataatgctt tgccagcagt acgtggtagc cacaattgca caatatattt    3240
tcttaaaaaa taccagcagt tactcatgga atatattctg cgtttataaa actagttttt    3300
aagaagaaat tttttttggc ctatgaaatt gttaaacctg aacatgaca ttgttaatca     3360 tataataatg attcttaaat gctgtatggt ttattattta aatgggtaaa gccatttaca    3420
taatatagaa agatatgcat atatctagaa ggtatgtggc atttatttgg ataaaattct    3480
caattcagag aaatcatctg atgtttctat agtcactttg ccagctcaaa agaaaacaat    3540
accctatgta gttgtggaag tttatgctaa tattgtgtaa ctgatattaa acctaaatgt    3600
tctgcctacc ctgttggtat aaagatattt tgagcagact gtaaacaaga aaaaaaaat    3660 catgcattct tagcaaaatt gcctagtatg ttaatttgct caaaatacaa tgtttgattt    3720
tatgcacttt gtcgctatta acatcctttt tttcatgtag atttcaataa ttgagtaatt    3780
ttagaagcat tattttagga atatatagtt gtcacagtaa atatcttgtt ttttctatgt    3840
acattgtaca aattttcat tcccttttgct ctttgtggtt ggatctaaca ctaactgtat     3900
tgttttgtta catcaaataa acatcttctg tggaccagga aaaaaaaaa aaaaaaa       3958

<210> SEQ ID NO 6
<211> LENGTH: 3812
<212> TYPE: DNA
<213> ORGANISM: Homo sapiens
<220> FEATURE:
<223> OTHER INFORMATION: HIF-1a cDNA variant 2

<400> SEQUENCE: 6
gtgctgcctc gtctgagggg acaggaggat caccctcttc gtcgcttcgg ccagtgtgtc      60
gggctgggcc ctgacaagcc acctgaggag aggctcggag ccgggcccgg accccggcga    120
ttgccgcccg cttctctcta gtctcacgag gggtttcccg cctcgcaccc ccacctctgg    180
acttgccttt ccttctcttc tccgcgtgtg gagggagcca gcgcttaggc cggagcgagc    240 ctggggccg cccgccgtga agacatcgcg gggaccgatt caccatggag ggcgccggcg    300
gcgcgaacga caagaaaaag ataagttctg aacgtcgaaa agaaaagtct cgagatgcag    360
ccagatctcg gcgaagtaaa gaatctgaag tttttttatga gcttgctcat cagttgccac    420
ttccacataa tgtgagttcg catcttgata aggcctctgt gatgaggctt accatcagct    480
atttgcgtgt gaggaaactt ctggatgctg tgatttgga tattgaagat gacatgaaag    540
cacagatgaa ttgcttttat ttgaaagcct tggatggttt tgttatggtt ctcacagatg    600
atggtgacat gatttacatt tctgataatg tgaacaaata catgggatta actcagtttg    660
aactaactgg acacagtgtg tttgatttta ctcatccatg tgaccatgag gaaatgagag    720
aaatgcttac acacagaaat ggccttgtga aaaggggtaa agaacaaaac acacagcgaa    780
gcttttttct cagaatgaag tgtacccctaa ctagccgagg aagaactatg aacataaagt    840
ctgcaacatg gaaggtattg cactgcacag gccacattca cgtatatgat accaacagta    900
accaacctca gtgtgggtat aagaaaccac ctatgacctg cttggtgctg atttgtgaac    960
ccattcctca cccatcaaat attgaaattc ctttagatag caagactttc ctcagtcgac   1020
```

```
acagcctgga tatgaaattt tcttattgtg atgaaagaat taccgaattg atgggatatg   1080
agccagaaga acttttaggc cgctcaattt atgaatatta tcatgctttg gactctgatc   1140
atctgaccaa aactcatcat gatatgttta ctaaaggaca agtcaccaca ggacagtaca   1200
ggatgcttgc caaagaggt ggatatgtct gggttgaaac tcaagcaact gtcatatata    1260
acaccaagaa ttctcaacca cagtgcattg tatgtgtgaa ttacgttgtg agtggtatta   1320
ttcagcacga cttgattttc tcccttcaac aaacagaatg tgtccttaaa ccggttgaat   1380
cttcagatat gaaaatgact cagctattca ccaaagttga atcagaagat acaagtagcc   1440
tctttgacaa acttaagaag gaacctgatg cttaactttt gctggcccca gccgctggag   1500
acacaatcat atctttagat tttggcagca acgacacaga aactgatgac cagcaacttg   1560
aggaagtacc attatataat gatgtaatgc tcccctcacc caacgaaaaa ttacagaata   1620
taaatttggc aatgtctcca ttacccaccg ctgaaacgcc aaagccactt cgaagtagtg   1680
ctgaccctgc actcaatcaa gaagttgcat taaaattaga accaaatcca gagtcactgg   1740
aactttcttt taccatgccc cagattcagg atcagacacc tagtccttcc gatggaagca   1800
ctagacaaag ttcacctgag cctaatagtc ccagtgaata ttgtttttat gtggatagtg   1860
atatggtcaa tgaattcaag ttggaattgg tagaaaaact ttttgctgaa gacacagaag   1920
caaagaaccc attttctact caggacacag atttagactt ggagatgtta gctccctata   1980
tcccaatgga tgatgacttc cagttacgtt ccttcgatca gttgtcacca ttagaaagca   2040
gttccgcaag ccctgaaagc gcaagtcctc aaagcacagt tacagtattc cagcagactc   2100
aaatacaaga acctactgct aatgccacca ctaccactgc caccactgat gaattaaaaa   2160
cagtgacaaa agaccgtatg gaagacatta aaatattgat tgcatctcca tctcctaccc   2220
acatacataa agaaactact agtgccacat catcaccata tagagatact caaagtcgga   2280
cagcctcacc aaaacagagca ggaaaaggag tcatagaaca gacagaaaaa tctcatccaa   2340
gaagccctaa cgtgttatct gtcgctttga gtcaaagaac tacagttcct gaggaagaac   2400
taaatccaaa gatactagct ttgcagaatg ctcagagaaa gcgaaaaatg gaacatgatg   2460
gttcactttt tcaagcagta ggaattattt agcatgtaga ctgctggggc aatcaatgga   2520
tgaaagtgga ttaccacagc tgaccagtta tgattgtgaa gttaatgctc ctatacaagg   2580
cagcagaaac ctactgcagg gtgaagaatt actcagagct ttggatcaag ttaactgagc   2640
tttttcttaa tttcattcct tttttttggac actggtggct cactacctaa agcagtctat   2700
ttatattttc tacatctaat tttagaagcc tggctacaat actgcacaaa cttggttagt   2760 tcaattttg atccccttc tacttaattt acattaatgc tctttttag tatgttcttt    2820 aatgctggat cacagacagc tcattttctc agttttttgg tatttaaacc attgcattgc   2880
agtagcatca ttttaaaaaa tgcaccttt tatttattta tttttggcta gggagtttat     2940 cccttttcg aattattttt aagaagatgc caatataatt tttgtaagaa ggcagtaacc    3000
tttcatcatg atcataggca gttgaaaaat ttttacacct tttttttcac attttacata   3060
aataataatg ctttgccagc agtacgtggt agccacaatt gcacaatata ttttcttaaa   3120
aaataccagc agttactcat ggaatatatt ctgcgtttat aaaactagtt tttaagaaga   3180 aattttttt ggcctatgaa attgttaaac ctggaacatg acattgttaa tcatataata   3240
atgattctta aatgctgtat ggtttattat ttaaatgggt aaagccattt acataatata   3300
gaaagatatg catatatcta gaaggtatgt ggcattatt tggataaaat tctcaattca   3360
gagaaatcat ctgatgtttc tatagtcact ttgccagctc aaaagaaaac aatacccta   3420
```

| | |
|---|---|
| gtagttgtgg aagtttatgc taatattgtg taactgatat taaacctaaa tgttctgcct | 3480 |
| accctgttgg tataaagata tttttgagcag actgtaaaca agaaaaaaaa aatcatgcat | 3540 |
| tcttagcaaa attgcctagt atgttaattt gctcaaaata caatgtttga ttttatgcac | 3600 |
| tttgtcgcta ttaacatcct ttttttcatg tagatttcaa taattgagta attttagaag | 3660 |
| cattattttta ggaatatata gttgtcacag taaatatctt gttttttcta tgtacattgt | 3720 |
| acaaattttt cattccttttt gctctttgtg gttggatcta acactaactg tattgttttg | 3780 |
| ttacatcaaa taaacatctt ctgtggacca gg | 3812 |

<210> SEQ ID NO 7
<211> LENGTH: 3973
<212> TYPE: DNA
<213> ORGANISM: Mus musculus
<220> FEATURE:
<223> OTHER INFORMATION: HIF-1a cDNA

<400> SEQUENCE: 7

| | |
|---|---|
| cgcgaggact gtcctcgccg ccgtcgcggg cagtgtctag ccaggccttg acaagctagc | 60 |
| cggaggagcg cctaggaacc cgagccggag ctcagcgagc gcagcctgca cgcccgcctc | 120 |
| gcgtcccggg ggggtcccgc ctcccacccc gcctctggac ttgtctcttt cccgcgcgc | 180 |
| gcggacagag ccggcgttta ggccgagcg agcccggggg ccgccggccg ggaagacaac | 240 |
| gcgggcaccg attcgccatg gagggcgccg gcggcgagaa cgagaagaaa aagatgagtt | 300 |
| ctgaacgtcg aaaagaaaag tctagagatg cagcaagatc tcggcgaagc aaagagtctg | 360 |
| aagtttttta tgagcttgct catcagttgc cacttcccca caatgtgagc tcacatcttg | 420 |
| ataaagcttc tgttatgagg ctcaccatca gttatttacg tgtgagaaaa cttctggatg | 480 |
| ccggtggtct agacagtgaa gatgagatga aggcacagat ggactgtttt tatctgaaag | 540 |
| ccctagatgg cttttgtgatg gtgctaacag atgacggcga catggtttac atttctgata | 600 |
| acgtgaacaa atacatgggg ttaactcagt ttgaactaac tggacacagt gtgtttgatt | 660 |
| ttactcatcc atgtgaccat gaggaaatga gagaaatgct tacacacaga aatggcccag | 720 |
| tgagaaaagg gaaagaacta acacacagc ggagcttttt tctcagaatg aagtgcaccc | 780 |
| taacaagccg gggaggacg atgaacatca agtcagcaac gtggaaggtg cttcactgca | 840 |
| cgggccatat tcatgtctat gataccaaca gtaaccaacc tcagtgtggg tacaagaaac | 900 |
| cacccatgac gtgcttggtg ctgatttgtg aacccattcc tcatccgtca atatattgaaa | 960 |
| ttccttttaga tagcaagaca tttctcagtc gacacagcct cgatatgaaa tttttcttact | 1020 |
| gtgatgaaag aattactgag ttgatgggtt atgagccgga agaacttttg ggccgctcaa | 1080 |
| tttatgaata ttatcatgct ttggattctg atcatctgac caaaactcac catgatatgt | 1140 |
| ttactaaagg acaagtcacc acaggacagt acaggatgct tgccaaaaga ggtggatatg | 1200 |
| tctgggttga aactcaagca actgtcatat ataatacgaa gaactcccag ccacagtgca | 1260 |
| ttgtgtgtgt gaattatgtt gtaagtggta ttattcagca cgacttgatt ttctcccttc | 1320 |
| aacaaacaga atctgtgctc aaaccagttg aatcttcaga tatgaagatg actcagctgt | 1380 |
| tcaccaaagt tgaatcagag gatacaagct gccttttga taagcttaag aaggagcctg | 1440 |
| atgctctcac tctgctggct ccagctgccg gcgacaccat catctctctg gattttggca | 1500 |
| gcgatgacac agaaactgaa gatcaacaac ttgaagatgt tccattatat aatgatgtaa | 1560 |
| tgtttcctc ttctaatgaa aaattaaata taaacctggc aatgtctcct ttaccttcat | 1620 |
| cggaaactcc aaagccactt cgaagtagtg ctgatcctgc actgaatcaa gaggttgcat | 1680 |

```
taaaattaga atcaagtcca gagtcactgg gactttcttt taccatgccc cagattcaag      1740
atcagccagc aagtccttct gatggaagca ctagacaaag ttcacctgag agacttcttc      1800
aggaaaacgt aaacactcct aacttttccc agcctaacag tcccagtgaa tattgctttg      1860
atgtggatag cgatatggtc aatgtattca agttggaact ggtggaaaaa ctgtttgctg      1920
aagcacagag ggcaaagaat ccattttcaa ctcaggacac tgatttagat ttggagatgc      1980
tggctcccta tatcccaatg gatgatgatt tccagttacg ttcctttgat cagttgtcac      2040
cattagagag caattctcca agccctccaa gtatgagcac agttactggg ttccagcaga      2100
cccagttaca gaaacctacc atcactgcca ctgccaccac aactgccacc actgatgaat      2160
caaaaacaga gacgaaggac aataaagaag atattaaaat actgattgca tctccatctt      2220
ctacccaagt acctcaagaa acgaccactg ctaaggcatc agcatacagt ggcactcaca      2280
gtcggacagc ctcaccagac agagcaggaa agagagtcat agaacagaca gacaaagctc      2340
atccaaggag ccttaagctg tctgccactt tgaatcaaag aaatactgtt cctgaggaag      2400
aattaaaccc aaagacaata gcttcgcaga atgctcagag gaagcgaaaa atggaacatg      2460
atggctccct ttttcaagca gcaggaattg gaacattatt gcagcaacca ggtgactgtg      2520
cacctactat gtcactttcc tggaaacgag tgaaaggatt catatctagt gaacagaatg      2580
gaacggagca aaagactatt attttaatac cctccgattt agcatgcaga ctgctggggc      2640
agtcaatgga tgagagtgga ttaccacagc tgaccagtta cgattgtgaa gttaatgctc      2700
ccatacaagg cagcagaaac ctactgcagg gtgaagaatt actcagagct ttggatcaag      2760
ttaactgagc gtttcctaat ctcattcctt ttgattgtta atgttttgt tcagttgttg      2820 ttgtttgttg ggttttttgtt tctgttggtt attttttggac actggtggct cagcagtcta      2880
tttatatttt ctatatctaa ttttagaagc ctggctacaa tactgcacaa actcagatag      2940
tttagttttc atcccctttc tacttaattt tcattaatgc tctttttaat atgttctttt      3000
aatgccagat cacagcacat tcacagctcc tcagcatttc accattgcat tgctgtagtg      3060
tcatttaaaa tgcacctttt tatttattta ttttttggtga gggagtttgt cccttattga      3120
attattttta atgaaatgcc aatataattt tttaagaaag cagtaaattc tcatcatgat      3180
cataggcagt tgaaaacttt ttactcattt ttttcatgtt ttacatgaaa ataatgcttt      3240
gtcagcagta catggtagcc acaattgcac aatatatttt ctttaaaaaa ccagcagtta      3300
ctcatgcaat atattctgca tttataaaac tagtttttaa gaaattttt ttggcctatg      3360 gaattgttaa gcctggatca tgaagcgttg atcttataat gattcttaaa ctgtatggtt      3420
tctttatatg ggtaaagcca tttacatgat ataagaaat atgcttatat ctggaaggta      3480
tgtggcattt atttggataa aattctcaat tcagagaagt tatctggtgt ttcttgactt      3540
taccaactca aaacagtccc tctgtagttg tggaagctta tgctaatatt gtgtaattga      3600
ttatgaaaca taaatgttct gcccaccctg ttggtataaa gacattttga gcatactgta      3660
aacaaacaaa caaaaaatca tgctttgtta gtaaaattgc ctagtatgtt gatttgttga      3720
aaatatgatg tttggttta tgcactttgt cgctattaac atccttttt catatagatt      3780 tcaataagtg agtaatttta gaagcattat tttaggaata tagagttgtc atagtaaaca      3840
tcttgttttt tctatgtaca ctgtataaat ttttcgttcc cttgctcttt gtggttgggt      3900
ctaacactaa ctgtactgtt ttgttatatc aaataaacat cttctgtgga ccaggaaaaa      3960
aaaaaaaaaa aaa                                                        3973
```

```
<210> SEQ ID NO 8
<211> LENGTH: 3718
<212> TYPE: DNA
<213> ORGANISM: Rattus norvegicus
<220> FEATURE:
<223> OTHER INFORMATION: HIF-1a cDNA

<400> SEQUENCE: 8
```

| | | | | | |
|---|---|---|---|---|---|
| gacaccgcgg | gcaccgattc | gccatggagg | gcgccggcgg | cgagaacgag | aagaaaaata | 60 |
| ggatgagttc | cgaacgtcga | aagaaaagt | ctagggatgc | agcacgatct | cggcgaagca | 120 |
| aagagtctga | agttttttat | gagcttgctc | atcagttgcc | acttcccac | aacgtgagct | 180 |
| cccatcttga | taaagcttct | gttatgaggc | tcaccatcag | ttacttacgt | gtgaggaaac | 240 |
| ttctaggtgc | tggtgatctt | gacattgaag | atgaaatgaa | agcacagatg | aactgctttt | 300 |
| atctgaaagc | cctggatggc | tttgttatgg | tgctaacaga | tgatggtgac | atgatttaca | 360 |
| tttctgataa | cgtgaacaaa | tacatggggt | tgactcagtt | tgaactaact | ggacacagtg | 420 |
| tgtttgattt | tacccatcca | tgtgaccatg | aggaaatgag | agaaatgctt | acacacagaa | 480 |
| atggcccagt | gagaagggg | aagaacaaa | acacgcagcg | aagctttttt | ctcagaatga | 540 |
| aatgtaccct | aacaagccgg | gggaggacga | tgaacatcaa | gtcagcaacg | tggaaggtgc | 600 |
| tgcactgcac | aggccacatt | catgtgtatg | ataccagcag | taaccagccg | cagtgtggct | 660 |
| acaagaaacc | gccctatgacg | tgcttggtgc | tgatttgtga | acccattcct | catccatcaa | 720 |
| acattgaaat | tcctttagac | agcaagacat | ttctcagtcg | acacagcctc | gatatgaaat | 780 |
| tttcttactg | tgatgaaagg | attactgagt | tgatgggtta | tgagccagaa | gaacttttgg | 840 |
| gccgttcaat | ttatgaatat | tatcatgctt | tggactctga | tcatctgacc | aaaactcatc | 900 |
| atgacatgtt | tactaaagga | caagtcacca | caggacagta | caggatgctt | gcaaaagag | 960 |
| gtggatatgt | ctgggttgag | actcaagcaa | ctgttatata | taatacgaag | aactctcagc | 1020 |
| cacagtgcat | tgtgtgtgtg | aattatgttg | taagtggtat | tattcagcac | gacttgattt | 1080 |
| tctccttca | acaaacagaa | tctgtcctca | aaccagttga | atcttcagat | atgaaaatga | 1140 |
| cccagctgtt | cactaaagtg | gaatctgagg | acacgagctg | cctcttcgac | aagcttaaga | 1200 |
| aagagcccga | tgccctgact | ctgctagctc | cagcggctgg | ggacacgatc | atatcactgg | 1260 |
| acttcggcag | cgatgacacg | gaaactgaag | accaacaact | tgaagatgtc | ccgttgtaca | 1320 |
| atgatgtaat | gttcccctct | tctaatgaga | aattaaatat | aaatctggca | atgtctccat | 1380 |
| tacctgcctc | tgaaactcca | aagccacttc | gaagtagtgc | tgatcctgca | ctgaatcaag | 1440 |
| aggttgcatt | gaagttagag | tcaagcccag | agtcactggg | actttctttt | accatgcccc | 1500 |
| agattcaaga | tcagccagca | agtccttctg | atggaagcac | tagacaaagc | tcacctgagc | 1560 |
| ctaacagtcc | cagtgagtac | tgcttttgatg | tggacagcga | tatggtcaat | gtattcaagt | 1620 |
| tggaactggt | ggaaaaactg | tttgctgaag | acacagaagc | gaagaatcca | ttttcagctc | 1680 |
| aggacactga | tttagacttg | gaaatgctgg | ctccctatat | cccaatggat | gatgatttcc | 1740 |
| agttacgttc | ctttgatcag | ttgtcaccat | tagagagcaa | ttctccaagc | cctccgagtg | 1800 |
| tgagcacagt | tacaggattc | cagcagaccc | agttacagaa | acctaccatc | actgtcactg | 1860 |
| ccaccgcaac | tgccaccact | gatgaatcaa | aagcagtgac | gaaggacaat | atagaagaca | 1920 |
| ttaaaatact | gattgcatct | ccaccttcta | cccaagtacc | tcaagaaatg | accactgcta | 1980 |
| aggcatcagc | atacagtggt | actcacagtc | ggacagcctc | accagacaga | gcaggaaaga | 2040 |
| gagtcatagga | aaaacagac | aaagctcatc | caaggagcct | taacctatct | gtcacttga | 2100 |
| atcaaagaaa | tactgttcct | gaagaagaat | taaacccaaa | gacaatagct | ttgcagaatg | 2160 |

-continued

```
ctcagaggaa gcgaaaaatg gaacatgatg gctccctttt tcaagcagca ggaattggaa      2220
cgttactgca gcaaccaggt gaccgtgccc ctactatgtc gctttcttgg aaacgagtga      2280
aaggatacat atctagtgaa caggatggaa tggagcagaa gacaattttt ttaatacect      2340 ctgatttagc atgtagactg ctggggcagt caatggatga gagtggatta ccacagctga      2400
ccagttacga ttgtgaagtt aatgctccca tacaaggcag cagaaaccta ctgcagggtg      2460
aagaattact cagagctttg gatcaagtta actgagcttt tcctaatctc attcctttga      2520
ttgttaattt ttgtgttcag ttgttgttgt tgtctgtggg gtttcgtttc tgttggttgt      2580
tttggacact ggtggctcag cagtctattt atattttcta tatctcattt agaggcctgg      2640
ctacagtact gcaccaactc agatagttta gtttgggccc cttcctcctt cattttcact      2700
gatgctcttt ttaccatgtc cttcgaatgc cagatcacag cacattcaca gctcccagc      2760 atttcaccaa tgcattgctg tagtgtcgtt taaaatgcac ctttttattt atttattttt      2820
ggtgagggag tttgtcccct tattgaattat ttttaatgaa atgccaatat aatttttta      2880 gaaggcagta aatcttcatc atgatgatag gcagttgaaa atttttta t cattttttc       2940 atgttttaca tgaaaataat gctttgccag cagtacatgg tagccacaat tgcacaatat      3000
attttcttaa aaataccagc agttactcat gcatatattc tgcatttata aaactagttt      3060
ttaagaagaa actttttttg gcctatggaa ttgttaagcc tggatcatga tgctgttgat      3120
cttataatga ttcttaaact gtatggtttc tttatatggg taaagccatt tacatgatat      3180
agagagatat gctatatct ggaaggtata tggcattat ttggataaaa ttctcaattg        3240
agaagttatc tggtgtttct ttactttacc ggctcaaaag aaaacagtcc ctatgtagtt      3300
gtggaagctt atgctaatat tgtgtaattg atattaaaca ttaatgttc tgcctatect      3360 gttggtataa agacattttg agcatactgt aaacaaaaaa atcatgcatt gttagtaaaa      3420
ttgcctagta tgttaatttg ttgaaaatac gatgtttggt tttatgcact ttgtcgctat      3480
taacatcctt ttttcatat agatttcaat aattgagtaa ttttagaagc attatttag       3540 aaatatagag ttgtcatagt aaacatcttg tttttttttc ttttttttcta tgtacattgt    3600 ataaattttt cattcccttg ctctttgtag ttgggtctaa cactaactgt actgttttgt     3660
tatatcaaat aaacatcttc tgtggaccag gaaaaaaaaa aaaaaaaaaa aaaaaaa        3718
```

<210> SEQ ID NO 9
<211> LENGTH: 213
<212> TYPE: PRT
<213> ORGANISM: Homo sapiens
<220> FEATURE:
<223> OTHER INFORMATION: VHL protein isoform 1

<400> SEQUENCE: 9

```
Met Pro Arg Arg Ala Glu Asn Trp Asp Glu Ala Glu Val Gly Ala Glu
1               5                   10                  15

Glu Ala Gly Val Glu Glu Tyr Gly Pro Glu Glu Asp Gly Gly Glu Glu
                20                  25                  30

Ser Gly Ala Glu Glu Ser Gly Pro Glu Glu Ser Gly Pro Glu Glu Leu
            35                  40                  45

Gly Ala Glu Glu Glu Met Glu Ala Gly Arg Pro Arg Pro Val Leu Arg
        50                  55                  60

Ser Val Asn Ser Arg Glu Pro Ser Gln Val Ile Phe Cys Asn Arg Ser
65                  70                  75                  80

Pro Arg Val Val Leu Pro Val Trp Leu Asn Phe Asp Gly Glu Pro Gln
                85                  90                  95
```

```
Pro Tyr Pro Thr Leu Pro Pro Gly Thr Gly Arg Arg Ile His Ser Tyr
            100                 105                 110

Arg Gly His Leu Trp Leu Phe Arg Asp Ala Gly Thr His Asp Gly Leu
        115                 120                 125

Leu Val Asn Gln Thr Glu Leu Phe Val Pro Ser Leu Asn Val Asp Gly
    130                 135                 140

Gln Pro Ile Phe Ala Asn Ile Thr Leu Pro Val Tyr Thr Leu Lys Glu
145                 150                 155                 160

Arg Cys Leu Gln Val Val Arg Ser Leu Val Lys Pro Glu Asn Tyr Arg
                165                 170                 175

Arg Leu Asp Ile Val Arg Ser Leu Tyr Glu Asp Leu Glu Asp His Pro
                180                 185                 190

Asn Val Gln Lys Asp Leu Glu Arg Leu Thr Gln Glu Arg Ile Ala His
            195                 200                 205

Gln Arg Met Gly Asp
        210

<210> SEQ ID NO 10
<211> LENGTH: 172
<212> TYPE: PRT
<213> ORGANISM: Homo sapiens
<220> FEATURE:
<223> OTHER INFORMATION: VHL protein isoform 2

<400> SEQUENCE: 10

Met Pro Arg Arg Ala Glu Asn Trp Asp Glu Ala Glu Val Gly Ala Glu
1               5                   10                  15

Glu Ala Gly Val Glu Glu Tyr Gly Pro Glu Glu Asp Gly Gly Glu Glu
            20                  25                  30

Ser Gly Ala Glu Glu Ser Gly Pro Glu Glu Ser Gly Pro Glu Glu Leu
        35                  40                  45

Gly Ala Glu Glu Glu Met Glu Ala Gly Arg Pro Arg Pro Val Leu Arg
    50                  55                  60

Ser Val Asn Ser Arg Glu Pro Ser Gln Val Ile Phe Cys Asn Arg Ser
65                  70                  75                  80

Pro Arg Val Val Leu Pro Val Trp Leu Asn Phe Asp Gly Glu Pro Gln
                85                  90                  95

Pro Tyr Pro Thr Leu Pro Pro Gly Thr Gly Arg Arg Ile His Ser Tyr
            100                 105                 110

Arg Val Tyr Thr Leu Lys Glu Arg Cys Leu Gln Val Val Arg Ser Leu
        115                 120                 125

Val Lys Pro Glu Asn Tyr Arg Arg Leu Asp Ile Val Arg Ser Leu Tyr
    130                 135                 140

Glu Asp Leu Glu Asp His Pro Asn Val Gln Lys Asp Leu Glu Arg Leu
145                 150                 155                 160

Thr Gln Glu Arg Ile Ala His Gln Arg Met Gly Asp
                165                 170

<210> SEQ ID NO 11
<211> LENGTH: 181
<212> TYPE: PRT
<213> ORGANISM: Mus musculus
<220> FEATURE:
<223> OTHER INFORMATION: VHL protein

<400> SEQUENCE: 11

Met Pro Arg Lys Ala Ala Ser Pro Glu Glu Ala Ala Gly Glu Pro Gly
1               5                   10                  15
```

```
Pro Glu Glu Met Glu Ala Gly Arg Pro Arg Pro Val Leu Arg Ser Val
            20                  25                  30

Asn Ser Arg Glu Pro Ser Gln Val Ile Phe Cys Asn Arg Ser Pro Arg
        35                  40                  45

Val Val Leu Pro Leu Trp Leu Asn Phe Asp Gly Glu Pro Gln Pro Tyr
    50                  55                  60

Pro Ile Leu Pro Pro Gly Thr Gly Arg Arg Ile His Ser Tyr Arg Gly
65                  70                  75                  80

His Leu Trp Leu Phe Arg Asp Ala Gly Thr His Asp Gly Leu Leu Val
                85                  90                  95

Asn Gln Thr Glu Leu Phe Val Pro Ser Leu Asn Val Asp Gly Gln Pro
            100                 105                 110

Ile Phe Ala Asn Ile Thr Leu Pro Val Tyr Thr Leu Lys Glu Arg Cys
        115                 120                 125

Leu Gln Val Val Arg Ser Leu Val Lys Pro Glu Asn Tyr Arg Arg Leu
    130                 135                 140

Asp Ile Val Arg Ser Leu Tyr Glu Asp Leu Glu Asp Tyr Pro Ser Val
145                 150                 155                 160

Arg Lys Asp Ile Gln Arg Leu Ser Gln Glu His Leu Glu Ser Gln His
                165                 170                 175

Leu Glu Glu Glu Pro
            180

<210> SEQ ID NO 12
<211> LENGTH: 185
<212> TYPE: PRT
<213> ORGANISM: Rattus norvegicus
<220> FEATURE:
<223> OTHER INFORMATION: VHL protein

<400> SEQUENCE: 12

Met Pro Arg Lys Ala Ala Ser Pro Glu Glu Ala Glu Arg Met Pro Gly
1               5                   10                  15

Ser Glu Glu Ile Glu Ala Gly Arg Pro Arg Pro Val Leu Arg Ser Val
            20                  25                  30

Asn Ser Arg Glu Pro Ser Gln Val Ile Phe Cys Asn Arg Ser Pro Arg
        35                  40                  45

Val Val Leu Pro Leu Trp Leu Asn Phe Asp Gly Glu Pro Gln Pro Tyr
    50                  55                  60

Pro Thr Leu Pro Pro Gly Thr Gly Arg Arg Ile His Ser Tyr Arg Gly
65                  70                  75                  80

His Leu Trp Leu Phe Arg Asp Ala Gly Thr His Asp Gly Leu Leu Val
                85                  90                  95

Asn Gln Thr Glu Leu Phe Val Pro Ser Leu Asn Val Asp Gly Gln Pro
            100                 105                 110

Ile Phe Ala Asn Ile Thr Leu Pro Val Tyr Thr Leu Lys Glu Arg Cys
        115                 120                 125

Leu Gln Val Val Arg Ser Leu Val Lys Pro Glu Asn Tyr Arg Arg Leu
    130                 135                 140

Asp Ile Val Arg Ser Leu Tyr Glu Asp Leu Glu Asp His Pro Asn Val
145                 150                 155                 160

Arg Lys Asp Ile Gln Arg Leu Thr Gln Glu His Leu Glu Asn Gln Ala
                165                 170                 175

Leu Gly Glu Glu Pro Glu Gly Val His
            180                 185
```

```
<210> SEQ ID NO 13
<211> LENGTH: 2968
<212> TYPE: DNA
<213> ORGANISM: Homo sapiens
<220> FEATURE:
<223> OTHER INFORMATION: VHL cDNA variant 1

<400> SEQUENCE: 13
cctcgcctcc gttacaacgg cctacggtgc tggaggatcc ttctgcgcac gcgcacagcc      60
tccggccggc tatttccgcg agcgcgttcc atcctctacc gagcgcgcgc gaagactacg     120
gaggtcgact cggagcgcg cacgcagctc cgccccgcgt ccgacccgcg gatcccgcgg     180
cgtccggccc gggtggtctg gatcgcggag ggaatgcccc ggagggcgga gaactgggac     240
gaggccgagg taggcgcgga ggaggcaggc gtcgaagagt acggccctga agaagacggc     300
ggggaggagt cgggcgccga ggagtccggc ccggaagagt ccgcccgga ggaactgggc     360
gccgaggagg agatggaggc cgggcggccg cggcccgtgc tgcgctcggt gaactcgcgc     420
gagccctccc aggtcatctt ctgcaatcgc agtccgcgcg tcgtgctgcc cgtatggctc     480
aacttcgacg gcgagccgca gccctaccca acgctgccgc tggcacggg ccgccgcatc     540
cacagctacc gaggtcacct ttggctcttc agagatgcag ggacacacga tgggcttctg     600
gttaaccaaa ctgaattatt tgtgccatct ctcaatgttg acggacagcc tatttttgcc     660
aatatcacac tgccagtgta tactctgaaa gagcgatgcc tccaggttgt ccggagccta     720
gtcaagcctg agaattacag agactggac atcgtcaggt cgctctacga agatctggaa     780
gaccacccaa atgtgcagaa agacctggag cggctgacac aggagcgcat tgcacatcaa     840
cggatgggag attgaagatt tctgttgaaa cttacactgt ttcatctcag cttttgatgg     900
tactgatgag tcttgatcta gatacaggac tggttccttc cttagtttca aagtgtctca     960
ttctcagagt aaaataggca ccattgctta aagaaagtt aactgacttc actaggcatt    1020
gtgatgttta ggggcaaaca tcacaaaatg taatttaatg cctgcccatt agagaagtat    1080
ttatcaggag aaggtggtgg cattttttgct tcctagtaag tcaggacagc ttgtatgtaa    1140
ggaggtttgt ataagtaatt cagtgggaat tgcagcatat cgtttaattt taagaaggca    1200
ttggcatctg cttttaatgg atgtataata catccattct acatccgtag cggttggtga    1260
cttgtctgcc tcctgctttg ggaagactga ggcatccgtg aggcagggac aagtctttct    1320
cctctttgag accccagtgc ctgcacatca tgagccttca gtcagggttt gtcagaggaa    1380
caaaccaggg gacactttgt tagaaagtgc ttagaggttc tgcctctatt tttgttgggg    1440
ggtgggagag gggaccttaa aatgtgtaca gtgaacaaat gtcttaaagg gaatcatttt    1500
tgtaggaagc attttttata attttctaag tcgtgcactt tctcggtcca ctcttgttga    1560
agtgctgttt tattactgtt tctaaactag gattgacatt ctacagttgt gataatagca    1620
ttttttgtaac ttgccatccg cacagaaaat acgagaaaat ctgcatgttt gattatagta    1680
ttaatggaca aataagtttt tgctaaatgt gagtatttct gttcctttt gtaaatatgt    1740
gacattcctg attgatttgg gttttttgt tgttgttgtt ttgttttgtt ttgttttttt    1800
gagatggagt ctcactcttg tcacccaggc tggagtgcag tggcgccatc tcggctcact    1860
gcaacctctg cctcctgggt tcacgtaatc ctcctgagta gctgggatta caggcgcctg    1920
ccaccacgct ggccaatttt tgtactttta gtagagacag tgtttcgcca tgttggccag    1980
gctggtttca aactcctgac ctcaggtgat ccgcccacct cagcctccca aaatggtggg    2040
attacaggtg tgtgggccac cgtgcctggc tgattcagca tttttatca ggcaggacca    2100
```

-continued

| | |
|---|---|
| ggtggcactt ccacctccag cctctggtcc taccaatgga ttcatggagt agcctggact | 2160 |
| gtttcatagt tttctaaatg tacaaattct tataggctag acttagattc attaactcaa | 2220 |
| attcaatgct tctatcagac tcagtttttt gtaactaata datttttttt tccacttttg | 2280 |
| ttctactcct tccctaatag cttttttaaaa aaatctcccc agtagagaaa catttggaaa | 2340 |
| agacagaaaa ctaaaaagga agaaaaaaga tccctattag atacacttct taaatacaat | 2400 |
| cacattaaca ttttgagcta tttccttcca gccttttttag ggcagatttt ggttggtttt | 2460 |
| tacatagttg agattgtact gttcatacag ttttataccc ttttttcattt aactttataa | 2520 |
| cttaaatatt gctctatgtt agtataagct tttcacaaac attagtatag tctcccttt | 2580 |
| ataattaatg tttgtgggta tttcttggca tgcatcttta attccttatc ctagcctttg | 2640 |
| ggcacaattc ctgtgctcaa aaatgagagt gacggctggc atggtggctc ccgcctgtaa | 2700 |
| tcccagtact ttgggaagcc aaggtaagag gattgcttga gcccagaact tcaagatgag | 2760 |
| cctgggctca tagtgagaac ccatctatac aaaaaattt taaaaattag catggcggca | 2820 |
| cacatctgta atcctagcta cttggcaggc tgaggtgaga agatcattgg agtttaggaa | 2880 |
| ttggaggctg cagtgagcca tgagtatgcc actgcactcc agcctggggg acagagcaag | 2940 |
| accctgcctc aaaaaaaaaa aaaaaaa | 2968 |

<210> SEQ ID NO 14
<211> LENGTH: 2845
<212> TYPE: DNA
<213> ORGANISM: Homo sapiens
<220> FEATURE:
<223> OTHER INFORMATION: VHL cDNA variant 2

<400> SEQUENCE: 14

| | |
|---|---|
| cctcgcctcc gttacaacgg cctacggtgc tggaggatcc ttctgcgcac gcgcacagcc | 60 |
| tccggccggc tatttccgcg agcgcgttcc atcctctacc gagcgcgcgc gaagactacg | 120 |
| gaggtcgact cgggagcgcg cacgcagctc cgccccgcgt ccgacccgcg gatcccgcgg | 180 |
| cgtccggccc gggtggtctg atcgcggag ggaatgcccc ggagggcgga gaactgggac | 240 |
| gaggccgagt aggcgcgga ggaggcaggc gtcgaagagt acggccctga agaagacggc | 300 |
| ggggaggagt cgggcgccga ggagtccggc ccggaagagt ccggcccgga ggaactgggc | 360 |
| gccgaggagg agatggaggc cgggcggccg cggcccgtgc tgcgctcggt gaactcgcgc | 420 |
| gagccctccc aggtcatctt ctgcaatcgc agtccgcgcg tcgtgctgcc cgtatggctc | 480 |
| aacttcgacg gcgagccgca gccctaccca acgctgccgc ctggcacggg ccgccgcatc | 540 |
| cacagctacc gagtgtatac tctgaaagag cgatgcctcc aggttgtccg gagcctagtc | 600 |
| aagcctgaga attacaggag actggacatc gtcaggtcgc tctacgaaga tctggaagac | 660 |
| cacccaaatg tgcagaaaga cctggagcgg ctgacacagg agcgcattgc acatcaacgg | 720 |
| atgggagatt gaagatttct gttgaaactt acactgtttc atctcagctt ttgatggtac | 780 |
| tgatgagtct tgatctagat acaggactgg ttccttcctt agtttcaaag tgtctcattc | 840 |
| tcagagtaaa ataggcacca ttgcttaaaa gaaagttaac tgacttcact aggcattgtg | 900 |
| atgtttaggg gcaaacatca caaaatgtaa tttaatgcct gcccattaga gaagtattta | 960 |
| tcaggagaag gtggtggcat ttttgcttcc tagtaagtca ggcagcttg tatgtaagga | 1020 |
| ggttttgtata agtaattcag tgggaattgc agcatatcgt ttaattttaa gaaggcattg | 1080 |
| gcatctgctt ttaatggatg tataatacat ccattctaca tccgtagcgg ttggtgactt | 1140 |
| gtctgcctcc tgctttggga agactgaggc atccgtgagg cagggacaag tctttctcct | 1200 |

-continued

| | |
|---|---|
| ctttgagacc ccagtgcctg cacatcatga gccttcagtc agggtttgtc agaggaacaa | 1260 |
| accagggac actttgttag aaagtgctta gaggttctgc ctctattttt gttgggggt | 1320 |
| gggagagggg accttaaaat gtgtacagtg aacaaatgtc ttaaagggaa tcattttgt | 1380 |
| aggaagcatt ttttataatt ttctaagtcg tgcactttct cggtccactc ttgttgaagt | 1440 |
| gctgttttat tactgtttct aaactaggat tgacattcta cagttgtgat aatagcattt | 1500 |
| ttgtaacttg ccatccgcac agaaaatacg agaaaatctg catgtttgat tatagtatta | 1560 |
| atggacaaat aagttttgc taaatgtgag tatttctgtt cctttttgta aatatgtgac | 1620 |
| attcctgatt gatttgggtt ttttgttgt tgttgttttg ttttgttttg ttttttgag | 1680 |
| atggagtctc actcttgtca cccaggctgg agtgcagtgg cgccatctcg gctcactgca | 1740 |
| acctctgcct cctgggttca cgtaatcctc ctgagtagct gggattacag gcgcctgcca | 1800 |
| ccacgctggc caattttttgt acttttagta gagacagtgt ttcgccatgt tggccaggct | 1860 |
| ggtttcaaac tcctgacctc aggtgatccg cccaccttcag cctcccaaaa tggtgggatt | 1920 |
| acaggtgtgt gggccaccgt gcctggctga ttcagcattt tttatcaggc aggaccaggt | 1980 |
| ggcacttcca cctccagcct ctggtcctac caatggattc atggagtagc ctggactgtt | 2040 |
| tcatagttttt ctaaatgtac aaattcttat aggctagact tagattcatt aactcaaatt | 2100 |
| caatgcttct atcagactca gttttttgta actaatagat tttttttcc acttttgttc | 2160 |
| tactccttcc ctaatagctt tttaaaaaaa tctccccagt agagaaacat ttggaaaaga | 2220 |
| cagaaaacta aaaggaaga aaaaagatcc ctattagata cacttcttaa atacaatcac | 2280 |
| attaacattt tgagctattt ccttccagcc tttttagggc agattttggt tggtttttac | 2340 |
| atagttgaga ttgtactgtt catacagttt tataccctt ttcatttaac tttataactt | 2400 |
| aaatattgct ctatgttagt ataagctttt cacaaacatt agtatagtct cccttttata | 2460 |
| attaatgttt gtgggtattt cttggcatgc atctttaatt ccttatccta gcctttgggc | 2520 |
| acaattcctg tgctcaaaaa tgagagtgac ggctggcatg gtggctcccg cctgtaatcc | 2580 |
| cagtactttg ggaagccaag gtaagaggat tgcttgagcc cagaacttca agatgagcct | 2640 |
| gggctcatag tgagaaccca tctatacaaa aaatttttaa aaattagcat ggcggcacac | 2700 |
| atctgtaatc ctagctactt ggcaggctga ggtgagaaga tcattggagt ttaggaattg | 2760 |
| gaggctgcag tgagccatga gtatgccact gcactccagc ctgggggaca gagcaagacc | 2820 |
| ctgcctcaaa aaaaaaaaaa aaaaa | 2845 |

<210> SEQ ID NO 15
<211> LENGTH: 2730
<212> TYPE: DNA
<213> ORGANISM: Mus musculus
<220> FEATURE:
<223> OTHER INFORMATION: VHL cDNA

<400> SEQUENCE: 15

| | |
|---|---|
| cgccttcaag ttgcccggag cgcgtctggg accggcagac ctgtcccgga gcgcgtagat | 60 |
| ccgcacgcac gcacgcgccg cccacgtcca gcttgcgaat ccgagggacc cgttccaata | 120 |
| atgccccgga aggcagccag tccagaggag gcggcggggg agcccggtcc tgaggagatg | 180 |
| gaggctgggc ggccgcggcc ggtgctcgcg tcggtgaact cgcgcgagcc ctctcaggtc | 240 |
| atcttctgca accgcagccc gcgcgtcgtg ctgcctttgt ggctcaactt cgacggcgag | 300 |
| cctcagccct acccgatctt accaccgggc accggccgcc gcatccacag ctaccgaggt | 360 |
| catctttggc tcttcaggga tgcggggacc catgatggac ttctggttaa ccaaacggag | 420 |

```
ctgtttgtgc catccctcaa tgtcgatgga cagcctattt ttgccaacat cacattgcca    480
gtgtataccc tgaaagagcg gtgccttcag gttgtgcgga gcctggtcaa gcctgagaac    540
tacaggagac tggacatcgt caggtcactc tatgaggatt tggaggacta cccaagtgtg    600
cggaaggaca tacagcgact gagccaagag caccttgaga gtcagcacct ggaagaggag    660
ccttgaagga gtccatggag attaagtgtt cctgagtttc agccttgatg gtccgagatt    720
gatctcacaca taggacaggt cactttcttt cagttttaaa atggttcatt cttggagtaa    780
aactatccat cacgtaaaag aaagttaact aacatccctg ggctttgtag tgtttaagaa    840
taaacatgca aagtgccact gcgtctgccc tttgtagagc actcacccga gggaggaaga    900
cgttttcagt tttgcttcct ggtgaggctg gaagttgagt gtaaggatga ctgtgtaata    960
agctcagcag caggagttgt actgtgtcct ttcatttgag cagagggctc ttgcttggga   1020
aggcagagaa ggcccttccc aaacgctggg acagacctcc tgtggaggcc cgctgcctaa   1080
agcgtggagt cttcagtcat gaatgttgga cgaagaaacc attggatgct tggtgggaga   1140
gttgggaggg cctggctctt tgtctgagga gagccttaag tgttcatgta aggaacagct   1200
tagcagcttc tgatttccca cgtcccagca cttttctctct gttttttatt ttattttga   1260
gacttttgta tagcccaggc cagcctcagt cactcagcag aggattcctg accctctggg   1320
attatgtctc ctgacattgg gaacacatgt gtgcacacag cctgctctgc tcttcctttt   1380
cccatgttga gacgggctcc tgctgtagtc ctgcctggcc tgagctggag tcggtcctgc   1440
ctcctgaccg accgtctggc tgcttttctaa gctgggtaga cttcccatac tcactgttac   1500
agacagttac agcagagaag aaccatcctt gtgtaagtct ggttttgaga gctcctgtct   1560
ctgaggaagc tgttggcagg agcagggatt tctgttcctt cttgtcagcc cctagcattc   1620
cactttgttt tggcaggcgc tggttctgct ttgtaggtgg aagtgaagct ccactcagcc   1680
acagactcca gacagtgggt cacagagcag tctggaatgt gtagcagtct tatggatggt   1740
cacagctttt cttacatatt catattctat caaacgtttt gtaaagtata atttttt att   1800
tattttaat cccctt agag aaaaagtaaa agtagagaag cctgggtatt gtgtacacaa   1860
cagaaaggac agtcaaggaa agggaagcag aaaggctctt atgtactctc agcttcatgc   1920
aaccccctgta actggccgca tatgtagggc atattttaat tggttaaagc agtttgttgt   1980
ggctgaggtc ataagatata tacagttttg tatcctgatt tttcactgaa cttcattgtt   2040
ttttgtttgc ttgcttttcc cttcttcttt gttttttgct ttattgagat agggtttctc   2100
tgtagcccag gctgtcctag aactcccttt gtagaccaaa catctgatta ctggcctcac   2160
atggagagat ctgtctctgc ttttccagcg ctgggattga agtaggccta atcttcatct   2220
aacttcttag cttgtctttt ccatgttact acacacactg tgtaaatacc agtgtgctac   2280
cctccttctt tgagggtgac tgtttgggagt atttgtccaa atcctgggct ccttgagtgc   2340
agactgatgc tctaagatca gcaaaatgac tgaactacat cctaacactt cccagtgtcc   2400
tctcagtgtc tcttcttatc tgcagcattg caggagtgaa gtggccacag accagtgtgg   2460
aggcctgtgt gtgggaagtc agcaggtgcc aagctattga acattggtt ttatttttt   2520
aaaccgatct ctgtctctaa aagatgtgat gtttgtgtta ttcagctgga agtttgaata   2580
ctgttctctg tgctgtccaa caagtgaaga gttatgaaat gagccacttg tcctgggaca   2640
tcctgtaatg agttcctcgg gcttttctcc tgtgagtttt ctgaaaaaag ctgacctttt   2700
tagtacaata aacggtgcta attgaaggaa                                    2730
```

<210> SEQ ID NO 16

<211> LENGTH: 2807
<212> TYPE: DNA
<213> ORGANISM: Rattus norvegicus
<220> FEATURE:
<223> OTHER INFORMATION: VHL cDNA

<400> SEQUENCE: 16

| | | | | | |
|---|---|---|---|---|---|
| ccgcgttaaa | gccggacgga | gtacttctat | tgctggcaga | cctgccccgg | agcgcgtaaa | 60 |
| cccgcacgct | cgcgccgccc | acgtccagct | cgcgaatccg | gaggcgtccg | gttccaataa | 120 |
| tgccccggaa | ggcagctagt | ccagaggagg | cagaaaggat | gccgggctct | gaagagatag | 180 |
| aggctgggcg | gccgcggccg | gttttacgct | ctgtgaactc | gcgcgaaccc | tctcaggtca | 240 |
| tcttctgcaa | ccgcagcccg | cgcgtcgtgc | tgcctttgtg | gctcaacttt | gatggtgagc | 300 |
| ctcagcccta | cccgacctta | ccaccgggca | ccggccgccg | catccacagc | taccgaggtc | 360 |
| acctttggct | cttcagggat | gcggggaccc | atgatggact | tctggttaac | caaacggaac | 420 |
| tgtttgtgcc | atccctcaat | gttgatggac | agcctatttt | tgccaacatc | acattgccag | 480 |
| tgtataccct | gaaagagcgg | tgccttcagg | ttgtacggag | cctggtcaag | cctgagaact | 540 |
| acaggaggct | ggacatcgtc | aggtcgctct | atgaagactt | ggaagaccac | ccaaatgtgc | 600 |
| ggaaagacat | acagcggctg | acccaagagc | acctcgagaa | tcaggccctg | ggagaggagc | 660 |
| ctgaaggagt | ccactgagat | tacttggtcc | tgaatttcgg | ccttgatggt | ctgaaatcga | 720 |
| tctacacata | ggacaggtca | cttctcttcg | gttttaaaat | ggttcattct | tggagtaaaa | 780 |
| tatccatcat | gtaaaagaaa | gttaactaac | atcactgagc | tttgtagtgt | ttaagactaa | 840 |
| acctgcaaag | tgccaccgag | tctgcccttt | ctagagcatt | catcagaaga | agctgttttc | 900 |
| agttttgctt | cctagtaagg | ctggatgttc | agcataagga | tgttagtgtg | agcgattcgc | 960 |
| gaggagttgc | tctgtgtcct | ctaatctgaa | gaatacagcc | tcgtatgaac | agagccccac | 1020 |
| cgctcacttg | gggaaggctg | agaaggcccc | aatgctggga | tggacatcct | gtagaggccc | 1080 |
| agtgcctaat | gtgtgtggag | tcttcagtca | gtgttggagg | aacaaaccat | tgggtactta | 1140 |
| gtgggagagt | tggagggcct | ggctctctgt | ctgaggaaat | cttaagtgta | cacgtaaagg | 1200 |
| aacaacttag | cagcttctgt | ttagaaagaa | ctttctcttg | agtttccatg | tctcagcact | 1260 |
| ttctttctac | tttgttagtt | tattttattt | tattttgag | acttgtgtag | cccaggtcag | 1320 |
| cctcagtcac | tccggagggg | atgctggtct | tgaattccgg | atcctctggg | agtgtgtcag | 1380 |
| cattgggagc | acatgggtcg | accacagtct | gctctgttct | tgcttttccc | attttgagac | 1440 |
| gggctcatac | tgtagccctg | cctggcctca | agctagagtc | agccctgtct | ccccacccag | 1500 |
| tctggctgct | tagactgggt | gggcttccca | tattcactgc | cccagacagc | agagacgagc | 1560 |
| tgtccttgtg | tttaggtctg | gttttgagag | ttccttctct | gaggaagctg | ctggcaggag | 1620 |
| cagggtttct | gttccttccc | gtcagcccct | agcattccag | ctgggcgccg | cactctgctt | 1680 |
| tggcaggcgc | tagttatgct | tcgatggggag | agggagtga | agctccctca | gccacacact | 1740 |
| ccaaaccatg | ggtcccagag | cagtctgcaa | tgagtagtag | tttgtgggca | gtcacagctt | 1800 |
| ttcttacata | ttcaaatatt | gatgttcact | acttctatca | aacattttgt | agaacataat | 1860 |
| tttttatttg | ttttttaattc | ctcagcagag | aaaaatgaga | gaagcttggg | cattgtgtgt | 1920 |
| ggcacacacc | agaaaggaca | gtcagctgag | agggtgcaga | aaggctcttg | tgcgctggct | 1980 |
| ctcagctgca | tgtagtcctg | taacccagtg | ttctctctag | tacacatttt | aattggttaa | 2040 |
| agcactttgt | cctggccgag | atcataaggt | atatacagtt | ttgtggcctg | attttcatt | 2100 |
| gaacttcatt | gttttgtttt | ccctctcttt | tcgttttgg | ttttgttttt | ggtttgtttt | 2160 |

```
ttgcttttg tttatcaag atagagtttc tctgtgtagc ccaggctgtc ctggaactcc    2220 cttgtagac caaacaactg attactggcc tcaaacggag atctgtctgc ctctgcctct   2280
ccagtgctgg gattgaagta tgcctaatct tcatctaact tagtaacttg tctttccat   2340 gttactgcac acactgtcta aattccggtg tgctagcctc tccctttgag ggtgactgtt   2400
gggagtattt gtctcagtcc tgggctcctt gagtgcagtc tgatgctcta agatcagcaa   2460
aatcactgaa cttaatactg acactcctgc cgccctctca gcgtctctcc ttagtctgca   2520
gcattccgtg agtgaagcgg cacaggccag tgtggagcct gtgtgtggga agtcagcagg   2580
tgccgagcta ttgcaacatt ggttttattt tttaagccta tctctgtctc taaaagatgt   2640
aatgtttgtc ttatttaact ggaagtttga atactgttct ctgtgcctta ggacatgagt   2700
cacttgtcct tgcacatcct gtaagtgtgt tcctcagact ttgtactctc ctttgagttc   2760
tctgaaaaag ctgacccttta gtacaataaa cggtgctaag tgaagga               2807
```

```
<210> SEQ ID NO 17
<211> LENGTH: 21
<212> TYPE: RNA
<213> ORGANISM: Homo sapiens
<220> FEATURE:
<223> OTHER INFORMATION: VHL siRNA

<400> SEQUENCE: 17
cggccuacgg ugcuggaggu u                                              21

<210> SEQ ID NO 18
<211> LENGTH: 21
<212> TYPE: RNA
<213> ORGANISM: Homo sapiens
<220> FEATURE:
<223> OTHER INFORMATION: VHL siRNA

<400> SEQUENCE: 18
gacuacggag gucgacucgu u                                              21

<210> SEQ ID NO 19
<211> LENGTH: 21
<212> TYPE: RNA
<213> ORGANISM: Homo sapiens
<220> FEATURE:
<223> OTHER INFORMATION: VHL siRNA

<400> SEQUENCE: 19
ugccccggag ggcggagaau u                                              21

<210> SEQ ID NO 20
<211> LENGTH: 21
<212> TYPE: RNA
<213> ORGANISM: Homo sapiens
<220> FEATURE:
<223> OTHER INFORMATION: VHL siRNA

<400> SEQUENCE: 20
cugggacgag gccgagguau u                                              21

<210> SEQ ID NO 21
<211> LENGTH: 16
<212> TYPE: PRT
<213> ORGANISM: Artificial Sequence
<220> FEATURE:
<223> OTHER INFORMATION: synthetic peptide; matched amino acid sequence
      for HIF-1a

<400> SEQUENCE: 21
```

```
Ser Ile Tyr Glu Tyr Tyr His Ala Leu Asp Ser Asp His Leu Thr Lys
1               5                   10                  15

<210> SEQ ID NO 22
<211> LENGTH: 27
<212> TYPE: PRT
<213> ORGANISM: Artificial Sequence
<220> FEATURE:
<223> OTHER INFORMATION: synthetic peptide; matched amino acid sequence
      for HIF-1a
<220> FEATURE:
<221> NAME/KEY: Xaa
<222> LOCATION: (4)..(4)
<223> OTHER INFORMATION: Xaa = unknown amino acid sequence

<400> SEQUENCE: 22

Pro Pro Met Xaa Thr Cys Leu Val Leu Ile Cys Glu Pro Ile Pro His
1               5                   10                  15

Pro Ser Asn Ile Glu Ile Pro Leu Asp Ser Lys
            20                  25

<210> SEQ ID NO 23
<211> LENGTH: 19
<212> TYPE: PRT
<213> ORGANISM: Artificial Sequence
<220> FEATURE:
<223> OTHER INFORMATION: synthetic peptide; matched amino acid sequence
      for HIF-1a
<220> FEATURE:
<221> NAME/KEY: Xaa
<222> LOCATION: (12)..(12)
<223> OTHER INFORMATION: Xaa = unknown amino acid sequence

<400> SEQUENCE: 23

Thr Phe Leu Ser Arg His Ser Leu Asp Met Lys Xaa Phe Ser Tyr Cys
1               5                   10                  15

Asp Glu Arg

<210> SEQ ID NO 24
<211> LENGTH: 11
<212> TYPE: PRT
<213> ORGANISM: Artificial Sequence
<220> FEATURE:
<223> OTHER INFORMATION: synthetic peptide; matched amino acid sequence
      for HIF-1a
<220> FEATURE:
<221> NAME/KEY: Xaa
<222> LOCATION: (3)..(3)
<223> OTHER INFORMATION: Xaa = unknown amino acid sequence

<400> SEQUENCE: 24

Thr Met Xaa Asn Ile Lys Ser Ala Thr Trp Lys
1               5                   10

<210> SEQ ID NO 25
<211> LENGTH: 14
<212> TYPE: PRT
<213> ORGANISM: Artificial Sequence
<220> FEATURE:
<223> OTHER INFORMATION: synthetic peptide; matched amino acid sequence
      for HIF-2a
<220> FEATURE:
<221> NAME/KEY: Xaa
<222> LOCATION: (7)..(7)
<223> OTHER INFORMATION: Xaa = unknown amino acid sequence

<400> SEQUENCE: 25

Glu Asn Leu Thr Leu Lys Xaa Asn Gly Ser Gly Phe Gly Lys
1               5                   10
```

```
<210> SEQ ID NO 26
<211> LENGTH: 11
<212> TYPE: PRT
<213> ORGANISM: Artificial Sequence
<220> FEATURE:
<223> OTHER INFORMATION: synthetic peptide; matched amino acid sequence
      for HIF-2a
<220> FEATURE:
<221> NAME/KEY: Xaa
<222> LOCATION: (2)..(2)
<223> OTHER INFORMATION: Xaa = unknown amino acid sequence

<400> SEQUENCE: 26

Met Xaa Arg Ser Ala Lys Asp Phe Gly Ala Arg
1               5                   10
```